US009302036B2

(12) United States Patent
Gerber et al.

(10) Patent No.: US 9,302,036 B2
(45) Date of Patent: Apr. 5, 2016

(54) BLOOD FLUID REMOVAL SYSTEM PERFORMANCE MONITORING

(75) Inventors: Martin Gerber, Maple Grove, MN (US); Suping Lyu, Maple Grove, MN (US); Bryant Pudil, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 706 days.

(21) Appl. No.: 13/424,517

(22) Filed: Mar. 20, 2012

(65) Prior Publication Data

US 2012/0273415 A1    Nov. 1, 2012

Related U.S. Application Data

(60) Provisional application No. 61/480,539, filed on Apr. 29, 2011, provisional application No. 61/480,544, (Continued)

(51) Int. Cl.
*B01D 61/32* (2006.01)
*B01D 61/24* (2006.01)
(Continued)

(52) U.S. Cl.
CPC ............ *A61M 1/1603* (2014.02); *A61B 5/0031* (2013.01); *A61B 5/026* (2013.01);
(Continued)

(58) Field of Classification Search
CPC ........... A61M 1/00; A61M 1/16; A61M 1/14; A61M 1/1613; A61M 1/342; A61M 2205/52; A61M 1/3609; A61M 1/1601; A61M 1/34; A61M 1/1647; A61M 2205/3334; A61M 2205/7563; A61M 2205/18; A61M 2205/70; A61M 2230/208; A61M 1/3607; A61M 2205/3351; A61M 2205/3523; A61M 2230/00; A61M 1/1603; A61M 1/1605; A61M 1/1607; A61M 2205/04; A61M 2205/3303; A61M 2230/207; A61M 2205/33; A61M 2205/60; A61M 2230/65; A61M 2202/0498; A61M 2205/50; B01D 61/32; B01D 2321/12; B01D 2321/40; B01D 65/02; B01D 61/00; A61B 2560/0223; A61B 5/0031; A61B 5/026; A61B 5/0537; A61B 5/145; A61B 5/14546; A61B 5/4848; A61B 5/6866; A61B 5/0295; A61B 5/053; A61B 5/14503; A61B 5/14539; A61B 5/4836; A61B 5/14535; A61B 5/4875; A61B 5/7282
USPC ............... 210/85, 87, 90, 96.1, 96.2, 97, 103, 210/105, 106, 108, 134, 143, 195.1, 195.2, 210/252, 257.1, 258, 321.6, 321.65, 321.69, 210/502.1, 636, 646, 650, 739, 741
See application file for complete search history.

(56) References Cited

U.S. PATENT DOCUMENTS 4,374,382 A    2/1983    Markowitz
4,556,063 A    12/1985    Thompson
(Continued)

FOREIGN PATENT DOCUMENTS

EP    1364666 A1    11/2003
EP    0906768 B1    2/2004
(Continued)

OTHER PUBLICATIONS

Overgaard, et al., Activity-induced recovery of excitability in K+-depressed rat soleus muscle, Am J Physiol Regulatory Integrative Comp Physiol 280: R48-R55 (2001).*
(Continued)

*Primary Examiner* — John Kim
(74) *Attorney, Agent, or Firm* — Hahn & Voight PLLC; Roger C. Hahn; Kenneth J. Collier

(57) ABSTRACT

Monitoring of the performance of a blood fluid removal medium of a blood fluid removal device includes monitoring of condition, such as fluid flow rate or concentration of blood waste product, downstream of the medium. Upstream monitoring of the condition may also be performed to enhance the ability to determine whether the blood fluid removal medium is performing within predetermined ranges.

22 Claims, 9 Drawing Sheets

Related U.S. Application Data filed on Apr. 29, 2011, provisional application No. 61/480,541, filed on Apr. 29, 2011, provisional application No. 61/480,535, filed on Apr. 29, 2011, provisional application No. 61/480,532, filed on Apr. 29, 2011, provisional application No. 61/480,530, filed on Apr. 29, 2011, provisional application No. 61/480,528, filed on Apr. 29, 2011.

(51) Int. Cl.

| | | |
|---|---|---|
| B01D 65/02 | (2006.01) |
| B01D 61/28 | (2006.01) |
| A61M 1/16 | (2006.01) |
| A61B 5/145 | (2006.01) |
| A61B 5/00 | (2006.01) |
| A61B 5/026 | (2006.01) |
| A61B 5/053 | (2006.01) |
| A61M 1/34 | (2006.01) |
| A61M 1/00 | (2006.01) |
| A61B 5/0295 | (2006.01) |
| A61M 1/14 | (2006.01) |
| B01D 61/00 | (2006.01) |
| A61M 1/36 | (2006.01) |

(52) U.S. Cl.
CPC .............. *A61B 5/0295* (2013.01); *A61B 5/053* (2013.01); *A61B 5/0537* (2013.01); *A61B 5/145* (2013.01); *A61B 5/14503* (2013.01); *A61B 5/14535* (2013.01); *A61B 5/14539* (2013.01); *A61B 5/14546* (2013.01); *A61B 5/4836* (2013.01); *A61B 5/4848* (2013.01); *A61B 5/4875* (2013.01); *A61B 5/6866* (2013.01); *A61B 5/7282* (2013.01); *A61M 1/00* (2013.01); *A61M 1/14* (2013.01); *A61M 1/16* (2013.01); *A61M 1/1601* (2014.02); *A61M 1/1605* (2014.02); *A61M 1/1607* (2014.02); *A61M 1/1613* (2014.02); *A61M 1/34* (2013.01); *A61M 1/342* (2013.01); *A61M 1/3607* (2014.02); *A61M 1/3609* (2014.02); *B01D 61/00* (2013.01); *B01D 61/32* (2013.01); *B01D 65/02* (2013.01); *A61B 2560/0223* (2013.01); *A61M 2202/0498* (2013.01); *A61M 2205/04* (2013.01); *A61M 2205/18* (2013.01); *A61M 2205/33* (2013.01); *A61M 2205/3303* (2013.01); *A61M 2205/3334* (2013.01); *A61M 2205/3523* (2013.01); *A61M 2205/50* (2013.01); *A61M 2205/52* (2013.01); *A61M 2205/60* (2013.01); *A61M 2205/70* (2013.01); *A61M 2230/00* (2013.01); *A61M 2230/207* (2013.01); *A61M 2230/208* (2013.01); *A61M 2230/65* (2013.01); *B01D 2321/12* (2013.01); *B01D 2321/40* (2013.01)

(56) References Cited

U.S. PATENT DOCUMENTS

| | | | |
|---|---|---|---|
| 4,562,751 A | 1/1986 | Nason | |
| 4,678,408 A | 7/1987 | Mason | |
| 4,685,903 A | 8/1987 | Cable | |
| 4,750,494 A | 6/1988 | King | |
| 5,080,653 A | 1/1992 | Voss | |
| 5,092,886 A | 3/1992 | Dobos-Hardy | |
| 5,097,122 A | 3/1992 | Colman | |
| 5,127,404 A | 7/1992 | Wyborny | |
| 5,305,745 A | 4/1994 | Zacouto | |
| 5,651,893 A * | 7/1997 | Kenley et al. ................. 210/636 |
| 5,683,432 A | 11/1997 | Goedeke | |
| 5,702,597 A * | 12/1997 | Chevallet ............ A61M 1/1656 |
| | | | 210/195.2 |
| 6,052,622 A | 4/2000 | Holmstrom | |
| 6,058,331 A | 5/2000 | King | |
| 6,230,059 B1 | 5/2001 | Duffin | |
| 6,248,093 B1 | 6/2001 | Moberg | |
| 6,321,101 B1 | 11/2001 | Holmstrom | |
| 6,362,591 B1 | 3/2002 | Moberg | |
| 6,363,279 B1 | 3/2002 | Ben-Haim | |
| 6,554,798 B1 | 4/2003 | Mann | |
| 6,555,986 B2 | 4/2003 | Moberg | |
| 6,589,229 B1 | 7/2003 | Connelly | |
| 6,602,399 B1 | 8/2003 | Fromherz | |
| 6,676,608 B1 | 1/2004 | Keren | |
| 6,711,439 B1 | 3/2004 | Bradley | |
| 7,077,819 B1 | 7/2006 | Goldau | |
| 7,131,956 B1 * | 11/2006 | Pirazzoli et al. .............. 604/6.09 |
| 7,674,231 B2 | 3/2010 | McCombie | |
| 7,754,852 B2 | 7/2010 | Burnett | |
| 7,756,572 B1 | 7/2010 | Fard | |
| 8,105,260 B2 * | 1/2012 | Tonelli et al. ................. 604/5.04 |
| 8,313,642 B2 | 11/2012 | Yu et al. | |
| 2002/0042561 A1 | 4/2002 | Schulman et al. | |
| 2004/0019312 A1 | 1/2004 | Childers | |
| 2004/0215090 A1 | 10/2004 | Erkkila | |
| 2005/0065760 A1 | 3/2005 | Murtfeldt | |
| 2005/0126961 A1 | 6/2005 | Bissler | |
| 2005/0234381 A1 | 10/2005 | Niemetz | |
| 2006/0025661 A1 | 2/2006 | Sweeney et al. | |
| 2006/0217771 A1 | 9/2006 | Soykan | |
| 2006/0226079 A1 | 10/2006 | Mori et al. | |
| 2006/0241709 A1 | 10/2006 | Soykan | |
| 2006/0264894 A1 | 11/2006 | Moberg | |
| 2007/0066928 A1 | 3/2007 | Lannoy | |
| 2007/0175827 A1 | 8/2007 | Wariar | |
| 2007/0215545 A1 | 9/2007 | Bissler | |
| 2007/0255250 A1 | 11/2007 | Moberg | |
| 2008/0021337 A1 | 1/2008 | Li | |
| 2008/0067132 A1 | 3/2008 | Ross et al. | |
| 2008/0215247 A1 | 9/2008 | Tonelli et al. | |
| 2009/0101577 A1 | 4/2009 | Fulkerson et al. | |
| 2009/0275849 A1 | 11/2009 | Stewart | |
| 2009/0275883 A1 | 11/2009 | Chapman et al. | |
| 2010/0094158 A1 | 4/2010 | Solem et al. | |
| 2010/0137693 A1 | 6/2010 | Porras | |
| 2010/0168546 A1 | 7/2010 | Kamath | |
| 2011/0066043 A1 | 3/2011 | Banet | |
| 2011/0077574 A1 | 3/2011 | Sigg | |
| 2011/0130666 A1 | 6/2011 | Dong | |
| 2012/0016228 A1 | 1/2012 | Kroh | |
| 2012/0273415 A1 | 11/2012 | Gerber | |
| 2012/0273420 A1 | 11/2012 | Gerber | |
| 2012/0277552 A1 | 11/2012 | Gerber | |
| 2012/0277604 A1 | 11/2012 | Gerber | |
| 2012/0277650 A1 | 11/2012 | Gerber | |
| 2012/0277655 A1 | 11/2012 | Gerber | |
| 2012/0277722 A1 | 11/2012 | Gerber | |

FOREIGN PATENT DOCUMENTS

| | | |
|---|---|---|
| EP | 2100553 A1 | 9/2009 |
| WO | 0066197 | 11/2000 |
| WO | 0066197 A1 | 11/2000 |
| WO | 0128860 A1 | 4/2001 |
| WO | 0170307 A1 | 9/2001 |
| WO | 0185295 | 11/2001 |
| WO | 0185295 A2 | 11/2001 |
| WO | 2004009158 | 1/2004 |
| WO | 2004030717 A2 | 4/2004 |
| WO | 2006011009 | 2/2006 |
| WO | 2007038347 | 4/2007 |
| WO | 2009026603 A1 | 3/2009 |
| WO | 2011025705 A1 | 3/2011 |
| WO | 2012148786 | 11/2012 |

(56) References Cited

FOREIGN PATENT DOCUMENTS

| WO | 2012148787 A1 | 11/2012 |
|---|---|---|
| WO | 2012148789 | 11/2012 |

OTHER PUBLICATIONS

Redfield, et al., Restoration of renal response to atrial natriuretic factor in experimental low-output heart failure, American Journal of Physiology—Regulatory, Integrative and Comparative Physiology, vol. 257, No. R917-R923, abstract (1989).*

Roberts M, The regenerative dialysis (REDY) sorbent system, Nephrology, 1998, 275-278 : 4.

Brynda, et. al., The detection of human β2-microglobulin by grating coupler immunosensor with three dimensional antibody networks, Biosensors & Bioelectronics, 1999, 363-368, 14(4).

Nedelkov, et. al., Design of buffer exchange surfaces and sensor chips for biosensor chip mass spectrometry, Proteomics, 2002, 441-446, 2(4).

Hemametrics, Crit-Line Hematocrit Accuracy, 2003, 1-5, vol. 1, Tech Note No. 11 (Rev. D).

Siegenthalar, et. al., Pulmonary fluid status monitoring with intrathoracic impedance, Journal of Clinical Monitoring and Computing, 2010, 449-451 : 24.

Wang, Fundamentals of intrathoracic impedance monitoring in heart failure, Am. J. Cardiology, 2007, 3G-310 : Suppl.

Bleyer, et. al., Sudden and cardiac death rates in hemodialysis patients, Kidney International, 1999, 1553-1559 : 55.

Zhong, et. al., Miniature urea sensor based on H(+)-ion sensitive field effect transistor and its application in clinical analysis, Chin. J. Biotechnol., 1992, 57-65, 8(1).

PCT/US2012/034331 International Search Report, Jul. 9, 2012.
PCT/US2012/034334 International Search Report, Jul. 6, 2012.
PCT/US2012/034335 International Search Report, Sep. 5, 2012.
PCT/US/2013/034327 International Search Report, Aug. 13, 2013.
PCT/US/2012/034329 International Search Report Dec. 3, 2012.
PCT/US2012/034331 Internarional Search Report, Jul. 9, 2012.

Lima, et al., An electrochemical sensor based on nanostructure hollsndite-type manganese oxide for detection of potassium ion, Sensors, 2009, 6613-8625, 9.

MacLean, et al., Effects of hindlimb contraction on pressor and muscle interstitial metabolite responses in the cat, J. App. Physiol., 1998, 1583-1592, 85 (4).

Overgaard. et al., Relations between excitability and contractility in rate soleus' muscle: role of the NA+—K+ pump and NA+—K—S gradients. Journal of Physiology, 1999, 215-225, 518(1).

PCT/US2012/034330, International Search Report, Aug. 28, 2012.
PCT/US2012/034332, International Search Report, Jul. 5, 2012.

Rogoza, et al., Validation of A&D UA-767 device for the self-measurement of blood pressure, Blood Pressure Monitoring, 2000, 227-231, 5(4).

Ronco, et al., "Cardiorenal Syndrome", J. Am. Coll. Cardiol., 2008, 1527-1539: 52(19).

Secemsky, et al., High prevalence of cardiac autonomic dysfunction and T-wave alternans in dialysis patients. Heart Rhythm, Apr. 2011, 592-598: vol. 8, No. 4.

Wei, et al., Fullerene-cryptand coated piezoelectric crystal urea sensor based on urease, Analytica Chimica Acta, 2001, 77-85:437.

Weiner, et al., Article: Cardiac Function and Cardiovascular Disease in Chronic Kidney Disease, Book: Primer on Kidney Diseases (Author: Greenberg, et al), 2009, 499-505, 5th Ed., Saunders Elsevier, Philadelphia, PA.

\* cited by examiner

BLOOD FLUID REMOVAL SYSTEM PERFORMANCE MONITORING

RELATED APPLICATION

This application claims priority to U.S. Provisional Application No. 61/480,539, U.S. Provisional Application No. 61/480,544, U.S. Provisional Application No. 61/480,541, U.S. Provisional Application No. 61/480,535, U.S. Provisional Application No. 61/480,532, U.S. Provisional Application No. 61/480,530, and U.S. Provisional Application No. 61/480,528, wherein each priority application was filed Apr. 29, 2011, wherein each priority application is hereby incorporated by reference in its entirety to the extent that it does not conflict with the disclosure presented herein.

FIELD

The present disclosure relates, among other things, to devices, systems and methods for monitoring performance of a blood fluid removal system, such as a hemodialysis system or an ultrafiltration system.

BACKGROUND

Many blood fluid removal systems, such as hemodialysis systems, ultrafiltration systems, hemodiafiltration systems, and the like, include components whose performance may deteriorate over time. For example, such systems often employ a medium for removal of waste products or fluid from the blood, which medium can foul and perform less efficiently over time. Such medium may include a sorbent, a filter, or the like. Over time, the medium tends to accumulate deposited proteins, blood cells and other material, which can interfere with the performance of the medium. It would be desirable to monitor the performance of the medium or other components to know when action should be taken in response to deteriorating medium, or other component, performance.

SUMMARY

This disclosure, among other things, describes devices, systems and methods for monitoring blood fluid removal medium performance. A variety of states, such as fluid flow rate, pressure, compound or solute concentration are described for monitoring medium performance. Monitoring of states downstream or downstream and upstream of the medium are described. In many embodiments, a blood fluid removal system is configured to monitor the medium performance based on sensed data acquired from the monitoring and to take corrective action if medium performance has deteriorated. Monitoring medium performance in a blood fluid removal system may be desirable for systems employing a blood fluid removal medium that is external to a patient or for systems that employ an implantable medium. In embodiments, corrective actions or compensatory actions may be taken based on the monitored medium performance. The actions may be taken before a blood fluid removal session begins or during a blood fluid removal session.

In various embodiments, a method for monitoring blood fluid removal medium performance of a blood fluid removal system is described herein. The system is configured such that untreated blood enters, or comes into contact with, the medium and reduced fluid or treated blood exits or leaves the medium. The method includes (i) monitoring an indicator of fluid flow, pressure or a level of a compound in removed fluid or treated blood downstream of the medium; and (ii) determining whether the medium is performing within predetermined parameters based on a value of the monitored indicator. The method may further include monitoring an indicator of fluid flow, pressure or a level of the compound in untreated blood upstream of the medium. A value of the monitored indicator obtained upstream of the medium may be compared to the value of the monitored indicator obtained downstream of the medium and the comparison may be used to determining whether the medium is performing within predetermined parameters. In some cases, the parameters may be based on the value of the monitored indicator obtained upstream of the medium.

In various embodiments, corrective or compensatory action may be taken if the system performance has diminished. For example, system parameters may be adjusted to return values of the monitored parameter to a desired range or to optimize performance. Alternatively, system parameters may be adjusted such that effective treatment is delivered despite the diminished system performance. In some situations, actions may be taken by the system to attempt to directly correct the cause of the diminished system performance.

A variety of embodiments of system configurations for carrying out performance monitoring of a blood fluid removal medium are also described herein.

In some embodiments, a method for monitoring the rate of blood flow into a blood fluid removal device is presented. Embodiments of actions that may be taken based on the monitored blood flow rate are described herein. The method includes monitoring rate of flow of blood, or an indicator thereof, entering a blood fluid removal device and determining whether the monitored flow rate or indicator is within a predetermined range. If the monitored flow rate or indicator is not within the predetermined range, a system parameter of the blood fluid removal device or a blood fluid removal session parameter is adjusted.

One or more embodiments of the systems, devices and methods described herein may provide one or more advantages over prior systems, devices and methods for blood fluid removal in patients. Such advantages will be apparent to those skilled in the art upon reading the following detailed description.

BRIEF DESCRIPTION OF THE DRAWINGS

The accompanying drawings, which are incorporated into and form a part of the specification, illustrate several embodiments of the present disclosure and, together with the description, serve to explain the principles of the disclosure. The drawings are only for the purpose of illustrating embodiments of the disclosure and are not to be construed as limiting the disclosure.

Figure 1:
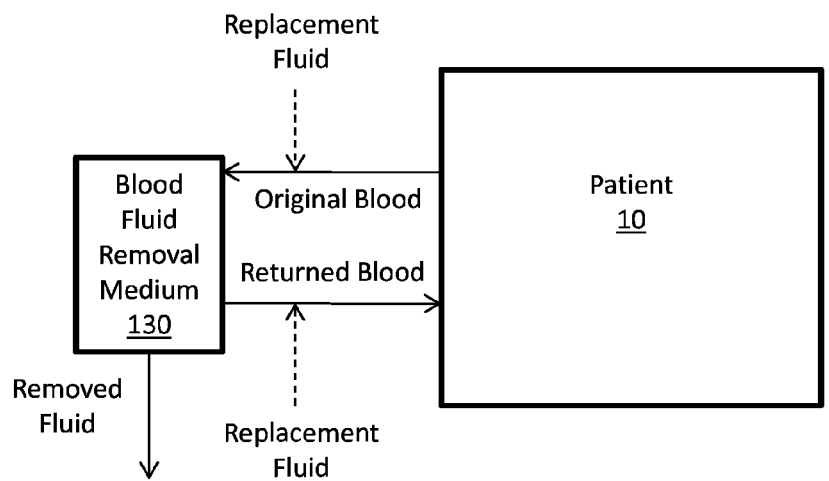
FIGS. 1-3 are schematic block diagrams showing interaction of blood fluid removal devices with a patient showing flow of blood (dashed arrows) and fluid (solid arrows), which blood fluid removal devices may be used in various embodiments described herein.

The schematic drawings presented herein are not necessarily to scale. Like numbers used in the figures refer to like components, steps and the like. However, it will be understood that the use of a number to refer to a component in a given figure is not intended to limit the component in another figure labeled with the same number. In addition, the use of different numbers to refer to components is not intended to indicate that the different numbered components cannot be the same or similar.

DETAILED DESCRIPTION

In the following detailed description, reference is made to the accompanying drawings that form a part hereof, and in which are shown by way of illustration several embodiments of devices, systems and methods. It is to be understood that other embodiments are contemplated and may be made without departing from the scope or spirit of the present disclosure. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise.

As used in this specification and the appended claims, the term "or" is generally employed in its sense including "and/or" unless the content clearly dictates otherwise.

As used herein, "have", "having", "include", "including", "comprise", "comprising" or the like are used in their open ended sense, and generally mean "including, but not limited to."

As used herein, a "patient for which a blood fluid removal session is indicated" is a patient that has undergone, is undergoing, or is likely to undergo at least one blood fluid removal session. In general, such patients are fluid overloaded patients, such as patients suffering from heart failure, chronic kidney disease, or acute renal failure. Often such patients are stage 3 to stage 5 chronic kidney disease patients, are unresponsive or under-responsive to diuretics, or the like.

As used herein, a "blood fluid removal process," or the like, refers to a process from which fluid is removed from blood of a patient and the blood is returned to the patient. In most cases (if not all), a blood fluid removal process also removes at least some waste products from the blood and returns cleaned blood to the patient. Examples of such processes include ultrafiltration, hemofiltration, hemodialysis, hemodiafiltration, peritoneal dialysis, and the like. Any patient for which blood fluid removal is indicated may benefit from the devices, systems and methods described herein.

This disclosure relates to, among other things, devices, systems and methods for monitoring performance of a blood fluid removal medium of a blood fluid removal device or system. The medium may include a semi-permeable membrane through which fluid and some compounds or solutes (but not blood cells) may pass. The medium may include a sorbent that is configured to adsorb fluid or compounds or solutes from blood, but is configured to allow blood cells to pass. Regardless of the medium employed, the present disclosure provides a variety of examples of how the performance of the medium may be monitored by monitoring a variety of states, such as fluid flow rate, pressure, concentration of certain compounds, or the like, downstream or downstream and upstream of the blood fluid removal medium.

Before discussing aspects of medium monitoring, a brief discussion of blood fluid removal systems and devices that may be employed in accordance with the teachings presented herein is provided. Any suitable device or system for removing fluid, or fluid and contaminants, from blood may be used in accordance with the teachings presented herein. The devices, or components thereof, may be traditional large counsel-type, wearable, or implantable.

Figure 2:
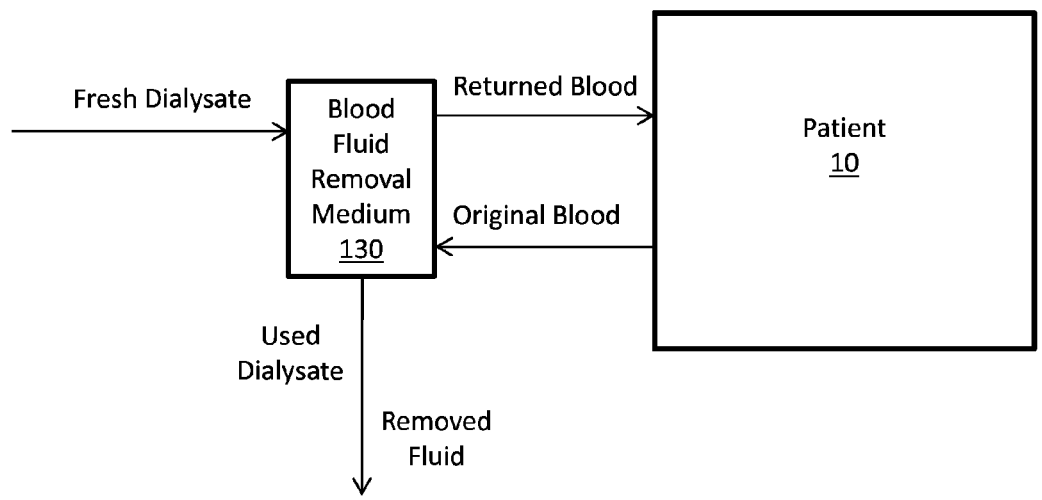
Figure 3:
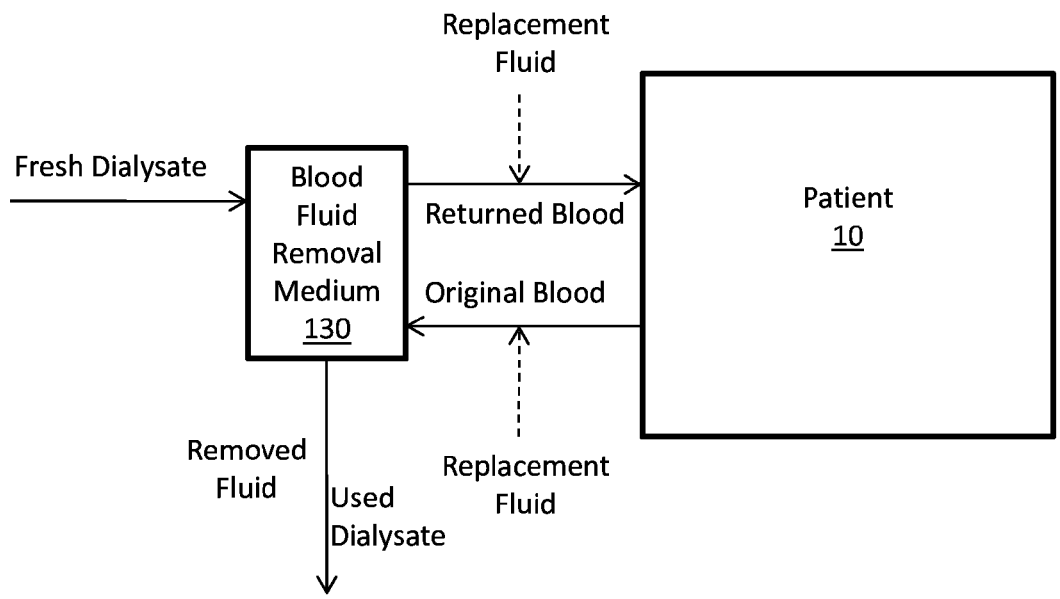

Block diagrams of some examples devices and systems are shown in FIGS. 1-3. As shown in FIG. 1, blood may be removed from a patient 10 and fluid, or fluid and contaminants, may be removed via a blood fluid removal medium 130 and returned to the patient 10. Removed fluid may be diverted. In some embodiments where the blood fluid removal medium 130, device, system, or components thereof, are implanted, the removed fluid may be diverted to the patient's bladder. Examples of blood fluid removal devices or systems that may operate as depicted in FIG. 1 are ultrafiltration and hemofiltration devices. Examples of such devices and components thereof that may be employed in accordance with the teachings presented herein are well known in the art. With some of such devices, replacement fluid may be introduced into the patient's blood if fluid is removed from the blood by the medium 130 at too great of a rate or amount. The replacement fluid may be added to the original blood before fluid removal or may be added to the blood after initial fluid removal and prior to return to the patient's cardiovascular system. Preferably, the replacement fluid is added after initial fluid removal. The replacement fluid may be configured to have a suitable pH buffer concentration and electrolyte concentrations.

As shown in the embodiment depicted in FIG. 2, dialysate may be employed to assist the blood fluid removal medium 130 in removal of contaminants from the patient's blood and in maintaining proper pH and electrolyte balance. Used dialysate and fluid removed from the blood may be diverted. In some embodiments, particularly where the blood fluid removal medium 130 or system or components thereof are wearable or implantable, the used dialysate and removed fluid (or a portion thereof) may be regenerated to produce fresh dialysate for re-use in the blood fluid removal process. One system for regeneration of dialysate is the REDY system, such as described in Roberts, M, "The regenerative dialysis (REDY) sorbent system," *Nephrology* 4:275-278, 1998, which system may be employed or readily modified for use in embodiments described herein.

Regardless of whether the dialysate is regenerated, systems and devices that operate in a manner shown in the embodiment of FIG. 2 include hemodialysis and hemodiafiltration systems. Examples of such devices and components thereof that may be employed in accordance with the teachings presented herein are well known in the art. It will be understood that peritoneal dialysis, where the dialysate is introduced into peritoneal cavity may also be employed.

As shown in FIG. 3, in cases where fluid from the blood is removed at too high of a rate, replacement fluid may be introduced into the patient's blood, upstream or downstream of the fluid removal medium 130, e.g. as described above with regard to FIG. 1.

Regardless of the device or blood fluid removal process employed, the performance of the medium may be monitored in accordance with the principles described herein. By way of example and with reference to FIG. 4, one or more sensors 200A-C may be employed to monitor the performance of the blood fluid removal medium 130. The sensors may be positioned to monitor upstream 200A or downstream 200B, 200C of the medium 130.

Any suitable sensor may be used. In embodiments, the sensor is configured to monitor an indicator of fluid flow rate. The sensor may employ any suitable flow meter, such as an acoustic Doppler velocimeter, an optical flow meter, a thermal flow meter, a Venturi meter, in-fluid paddle type meter, or the like. In some embodiments, a pressure sensor is used and the flow is calculated based on the pressure and the known diameter of the tubing through which the fluid flows. Such flow meters and components thereof are known in the art and can be readily adapted for use herein.

In embodiments, one or more pressure sensor is used to measure differential pressure across the medium, or a portion thereof (such as a membrane), for purposes of monitoring membrane performance. For example, an increased relative pressure upstream of the medium, or portion thereof, may indicate decreased performance of the medium (e.g., fouling). By way of further example, a decreased relative upstream pressure may be indicative of a rip or tear in, for example, a membrane.

In embodiments, the sensor is configured to monitor an indicator of a compound in blood or in fluid removed from the blood. The sensors may be configured to monitor components of blood that are configured to be removed during some blood fluid removal processes, such as hemodialysis. Examples of such compounds include urea, creatinine, sulfate, phosphate, β-2-microglobulin, or the like. Sensors capable of measuring such compounds are known in the art and can be readily adapted for used herein. For example, Nova Biomedical manufactures a variety of sensors capable of detecting components in blood such as creatinine, phosphate, urea and the like, which sensors can be employed or adapted for use herein. Other urea sensor detection technology that may be employed or adapted for used herein is described by Zhong et al., Clin. J. Biotechnol. 1992; 8(1):57-65. β-2-microglobulin sensor detection technology that may be employed or adapted for used herein is described by Brynda et al., Biosens Bioelectron. 1999; 14(4):363-8 and by Nedelkov et al., Proteomics. 2002; 2(4):441-6. Of course, any suitable sensor technology may be employed.

In some embodiments, a system will include redundant sensors on the same upstream or downstream line to improve accuracy and reliability. In some embodiments, a sensor may have more than one transducer or sensing mechanism to detect more than one compound in blood or to detect a compound in blood and flow rate. In some embodiments, sensors for the same compound may be configured to accurately detect different ranges of concentrations of the compound. In embodiments, more than one transducer is present in a single unit. This allows for convenient data collection and circuitry, as all the data may be collected in one place at the same time.

Figure 4:
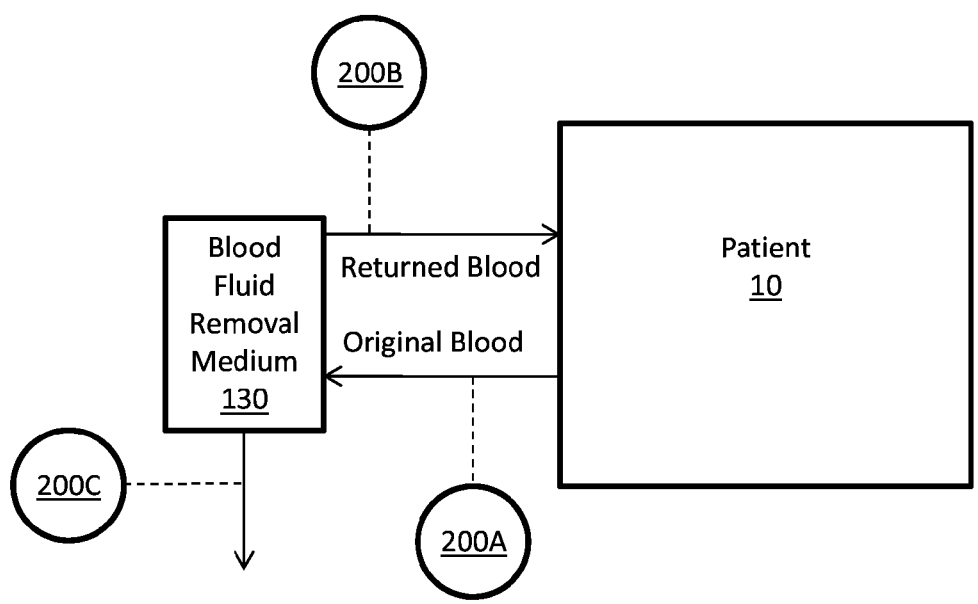
FIG. 4 is a schematic block diagram of an embodiment of a blood fluid monitoring device and associated sensors.

Still with reference to FIG. 4, a downstream sensor 200B, 200C is employed to monitor flow rate, pressure or a compound in the removed fluid or blood to monitor the performance of the medium. By way of example, if the blood fluid removal medium 130 contains a semi-permeable membrane (as shown in, for example FIG. 5 and discussed below), sensor 200C may be used to monitor fluid flow exiting or after having exited the medium 130. If the membrane is performing within acceptable parameters, the fluid flow rate should be higher than if the membrane is fouled. If the membrane is ripped, torn, or the like, fluid flow detectable by sensor 200C may be higher than a predetermined threshold (which may be based on the settings of the system, as will be discussed in more detail below). In embodiments, flow rate is also detected by sensor 200A upstream of the medium 130. As the flow rate detected by sensor 200C downstream of the medium 130 is a function of the flow rate upstream of the medium 130, the flow rates upstream and downstream may be compared to determine whether the membrane is functioning properly. In embodiments, the measured flow rates upstream and downstream are used to maintain system performance. By keeping flow rates constant (by adjusting various system parameters) the system performance may be maintained. However, in cases where too much pressure is applied to maintain the flow rate, blood cells can be damaged. However, the system can monitor such parameters to avoid situations where blood is exposed to undesirably high pressure.

In embodiments where the medium includes a sorbent, flow rate detected by sensor 200B downstream of the medium 130 may provide information regarding the performance of the medium 130, with flow rates being higher, but not too high, when performing acceptably and lower when fouled. Flow rates that are too high; e.g., higher than a predetermined threshold, may be indicative of channeling. Flow rate detected by sensor 200A may be used in combination with data regarding flow rate detected by sensor 200B to enhance the determination as to whether the sorbent medium 130 is performing within acceptable ranges. Pressure differentials may similarly be employed for determining performance of the medium 130. For example, pressure above a predetermined threshold value may be indicative of fouling, and pressure below a predetermined threshold value may be indicative of channeling. In either case, such out of range pressure values; i.e. above an upper threshold vale or below a lower threshold value, may indicate poor performance or failure of the sorbent medium.

In embodiments, one or more of the sensors 200A-C are configured to monitor an indicator of a compound in the blood or fluid removed from the blood. Downstream sensors 200B-C or downstream and upstream 200A sensors may be employed for this purpose. The levels of waste products may be higher in the blood at the beginning of a blood fluid removal session and lower at the end. Thus, it may be expected that the concentration of waste product detected by sensor 200C may be high in the beginning of the session and lower at the end of the session. Similarly, the rate of change in the concentration of waste product removal would be expected to be higher at the beginning of a session and lower at the end of a session. The expected changes in amounts and rates, as detected by sensor 200C, may be used to determine whether the medium 130 is functioning properly.

Similarly, the presence of waste products in returned blood detectable by sensor 200A or 200B should be higher towards the beginning of a blood fluid removal session than towards the end of the session, and the rate of change should be higher towards the beginning of a blood fluid removal session than towards the end of the session. The expected changes in amounts and rates, as detected by sensor 200A or 200B, may be used to determine whether the medium 130 is functioning properly.

In embodiments, sensor 200A is used in combination with sensor 200B or 200C to determine whether the medium 130 is functioning properly. As the amount of a waste product detectable by a downstream sensor 200B, 200C is a function of the amount of the waste product in the upstream blood, which is detectable by sensor 200A, values obtained by the upstream 200A and downstream 200B, 200C may be compared to determine whether the membrane is functioning properly.

It will be understood that the description with regard to the system shown in FIG. 4 is applicable to a system that employs dialysate. In such systems, flow rate of removed fluid from the blood may be difficult to detect from the downstream sensor 200C due to the relative high flow volume of used dialysate through the outlet of the medium 130. However, the downstream flow sensor 200C may be advantageously used with systems that do not employ dialysate, such as ultrafiltration systems. Pressure sensors upstream and downstream of the medium or configured to measure a pressure differential across the membrane may be useful for systems that do employ dialysate and systems that do not employ dialysate.

It will also be understood that used dialysate may dilute compounds present in fluid removed from the blood. However, such compounds should still be detectable by a sensor 200C positioned at or downstream of an outlet of the medium 130 as depicted in FIG. 4. Accordingly, the sensor 200C is preferably configured to detect lower concentrations of the compound of interest than a similar sensor in, for example, an ultrafiltration system.

In embodiments, sensor 200A may measure blood flow rate or an indicator of flow rate, such as pressure. The rate of blood flow into the medium 130 may affect the performance of the system or blood fluid removal session. For example, if blood flow rate from the patient is low, it may be desirable to extend session time or increase the fluid removal rate per unit of blood. A variety of factors may influence blood flow rate into the system, such as needle placement, patient condition variability, blood line variability or the like. Regardless of the cause of blood flow variability, the system or session may be adjusted to account for such variability. In embodiments, parameters such as blood flow rate or membrane performance may be evaluated or analyzed prior to, or at the beginning of, a blood fluid removal session so that proper session or system parameters may be set prior to or at the beginning of the session. Of course, such parameters may be monitored during a session so that parameters may be appropriately changed, as needed or desired.

Figure 5:
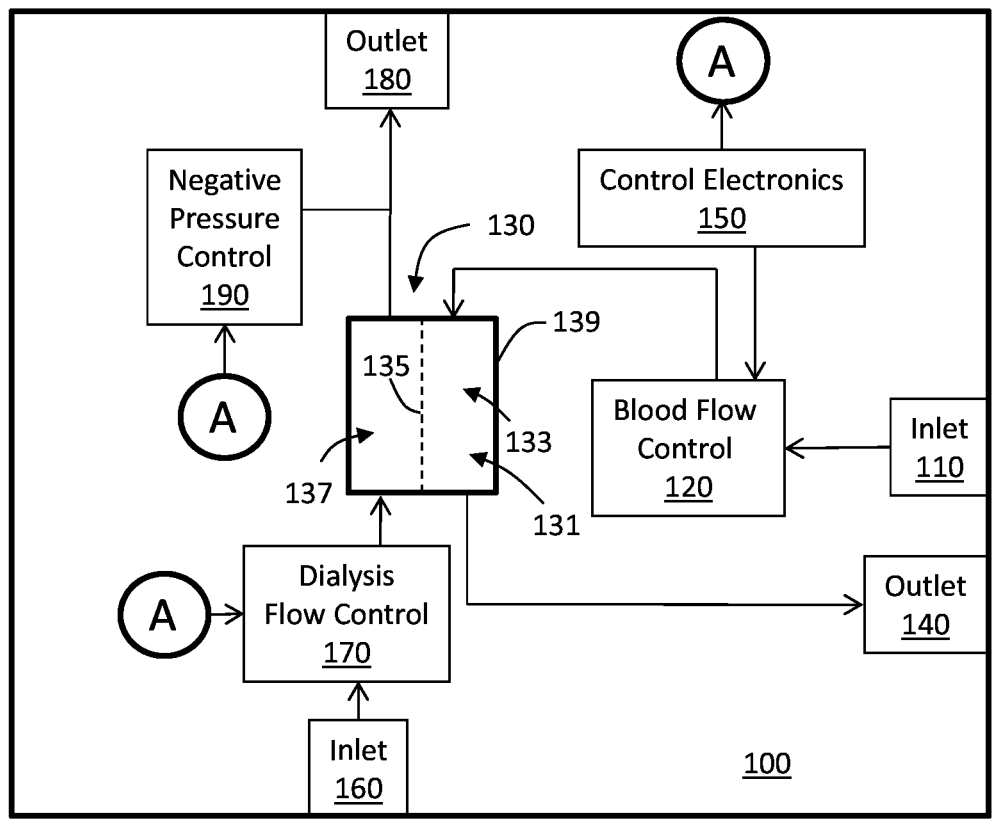
FIGS. 5-6 are schematic block diagrams showing some selected components of embodiments of blood fluid removal devices.

For purposes of example, some components of a generic hemodialysis system 100 are shown in FIG. 5. It will be understood that many of the concepts discussed below with regard to FIG. 5 are applicable to blood fluid removal devices other than hemodialysis devices. In the depicted embodiment, a blood fluid removal device 100 may include one or more control elements 120, 170, 190 that can affect the flow rates of fluid or blood or the blood fluid removal rate.

In the embodiment depicted in FIG. 5, the device 100 has an inlet 110 for receiving blood from a patient, a blood flow control element 120 in communication with the inlet 110 and configured to control the rate at which blood flows through medium 130 for removing fluid and contaminates from the blood. The device also includes an outlet 140 in communication with the medium 130 for returning blood to the patient. In the depicted embodiment, the medium 130 component has a housing 139 defining a major chamber 131. A semipermeable filter 135, such as a hemodialysis or hemodiafiltration filter, sealingly divides the major chamber into two minor chambers 133, 137; one 133 for blood flow 133 and the other 137 for dialysate flow (as well as fluid and waste that passes through the filter 135).

The device 100 has an inlet 160 for receiving fresh dialysate. Inlet 160 is in communication with a dialysis flow control element 170 for controlling the rate at which dialysis is introduced into the dialysis flow compartment 137 of the medium 130 component. The device also has an outlet 180 in communication with the medium 130 for diverting used dialysate and fluid removed from the blood out of the device. In the depicted embodiment, the device 100 also includes a negative pressure control element 190 in communication with the dialysate compartment 137 of the medium component 130 component, as needed or desired.

The device 100 also includes control electronics 150, which may include a processor, memory, etc., operably coupled to, and configured to control, the blood flow control element 120, the dialysis flow control element 170, and the negative pressure control element 190. Through control of one or more of the control elements, 120, 170, 190, the control electronics 150 can adjust the rate at which fluid is removed from the blood of the patient. For example, altering the flow rate of the blood (via the blood flow control element 120) through the medium component 130 may alter fluid clearance across the membrane. Similarly, adjusting flow of dialysate (via dialysis flow control element 170) through the medium component 130 may adjust the rate of fluid clearance across the membrane. Similarly, negative pressure (via negative pressure control element 190) may be applied on the dialysate compartment side 137 of the membrane 135 and may result in greater fluid clearance across the membrane due to convective forces. It will be understood that a device 100 need not have all of the controllable elements (120, 170, 190) depicted in FIG. 5 to effectively control rate of fluid removal from blood based on data from sensors that monitor indicators of tissue fluid volume and blood fluid volume.

Any suitable blood flow control elements 120 may be used to control flow of blood through the membrane component 130. For example, a variable or adjustable rate pump may be employed. Alternatively or in addition, a series of electronically controllable valves in communication flow paths having differing resistance to flow may be employed (in such cases the flow restrictors would preferably be downstream of the medium component 130). Dialysis flow control element 170 may contain similar components or be similarly configured to blood flow control element 120. The negative pressure control element 120 may include a vacuum pump or the like.

Figure 6:
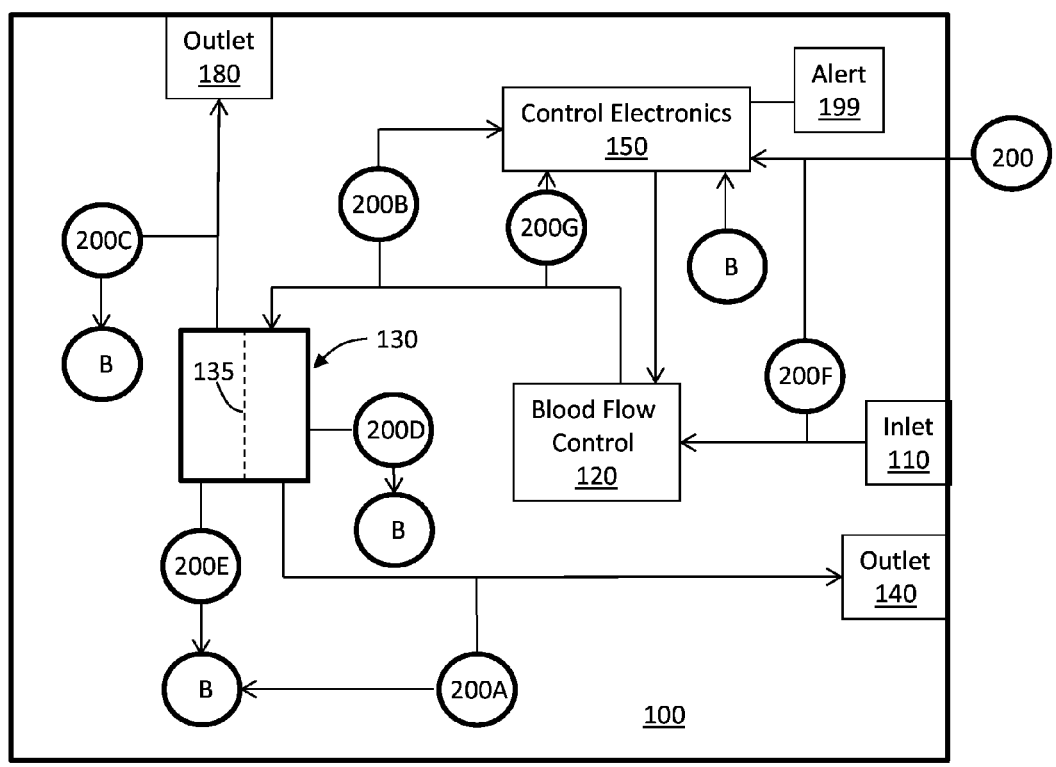

Referring now to FIG. 6, an embodiment of the device 100 shown in FIG. 5 is illustrated with positioning of sensors 200A-F. Like numbers in FIG. 6 refer to the same or similar components to those described above with regard to FIG. 5. For purposes of convenience, some of the components in FIG. 5 are omitted in FIG. 6. The device 100 in FIG. 6 also shows alert circuit 199 operably coupled to control electronics 150, which may be present in a device according to FIG. 5. If the control electronics 150 determine that the medium 130 or other system parameters are operating outside of an acceptable range, control electronics 150 can cause alert circuit 199 to notify a patient or healthcare provider to the issue. The alert circuit 199 may include components for an audible alarm, a display or the like. If the device 100 is implantable, the device may also include a telemetry circuit (not shown) for wireless communication with external devices, which can also provide alarms or alerts, if needed or desired.

The sensors 200A-C depicted in FIG. 6 may be sensors 200A-C as described above with regard to FIG. 4, except that the sensors in FIG. 6 are housed within device 100. That is, sensor 200B may be an upstream flow or pressure sensor or sensor for detecting a component of blood, and sensors 200A, 200C may be downstream flow or pressure sensors or sensors for detecting a component of blood as described above. The sensors are operably coupled to control electronics 150, which can acquire data from sensors 200A-C and determine whether the medium 130 is operating within predetermined acceptable ranges (e.g., as discussed above with regard to FIG. 5).

Control electronics 150 may also be operably coupled to one or more sensors 200 external to device 100, such as sensors 200A-C as discussed above with regard to FIG. 4.

The device 100 depicted in FIG. 6 also includes sensors 200D-E, which are pressure sensors, operably coupled to the control electronics 150. The pressure sensors 200D-E are configured to measure the pressure differential across the membrane 135. One of the sensors 200E is in communication with the blood fluid compartment (minor chamber 133 as depicted in FIG. 5), and the other is in communication with the dialysate compartment (minor chamber 137 as depicted in FIG. 5). The control electronics 150 may use data acquired from sensors 200D-E to determine whether the membrane 135 is operating acceptably based on other system parameters (such as settings of blood flow control element 120, dialysate flow control element 170, negative pressure control element 190, or the like). Alternatively or in addition, control electronics 150 may use information regarding the pressure differential across membrane 135 to assist in determining whether data acquired from one or more other sensor 200, 200A-C is indicative of the membrane 135 operating within normal parameters.

One or more sensor 200, 200A-E may be employed for purposes of monitoring the performance of the medium 130 depicted in FIG. 6. It will be understood that not all of the depicted sensors 200, 200A-E need to be present, although they may all be present.

If the control electronics 150 determine that the medium component 130 is operating outside of an acceptable range, control electronics 150 may cause an alert to be issued via alert circuit 199. Alternatively or in addition, control electronics 150 may adjust one or more system parameters (e.g., blood flow control element 120, dialysate flow control element 170, negative pressure control element 190, or the like) to attempt to bring medium component 130 back within acceptable parameters.

For example, the flow rate upstream and downstream of the medium may be maintained by adjusting suitable system parameters to maintain the performance of the medium. In some cases, the pressure differential across the membrane is adjusted to compensate for some degree of membrane performance deterioration (e.g., membrane slightly fouled) or some other system performance issue, such as a pinched but not completely occluded tube, or the like. Through monitoring as described herein, system performance may be maintained despite potential issues with some system components (fouled membrane, pinched tube, etc.) by compensating with system parameter adjustments to achieve a desired performance parameter (e.g., flow downstream of medium). However, in some cases, overcompensation (e.g., too much pressure on blood side of membrane to drive fluid across membrane) can be detrimental to the system or the blood (e.g., excessive pressure on blood can damage cells). Accordingly, limits on compensation may be set and monitored by the system.

In embodiments, the system is operated despite the performance parameters being out of a desired range. For example, if the performance of the system has deteriorated to a point where desired levels of, for example, pressure differential across a membrane, downstream flow rate, etc. are not achievable, the length of a blood fluid removal session may be extended so that a sufficient amount of fluid is removed from the patient despite the sub-optimal system performance.

In embodiments, corrective action to address the cause or source of the diminished system performance may be taken. For example, if the monitored parameters are indicative of the membrane fouling (e.g., pressure differential, flow rate or concentration of chemical species indicates fouling), the membrane may be effectively backwashed to de-foul the membrane. In systems that employ dialysate, pulses of increased flow or increased flow for sustained periods of time can be used to force proteins, or other foulants, that may have deposited on the blood side of the membrane back into the blood to increase the performance of the membrane. If the system has reached dialysate flow limits (e.g., limits due to safety or maximal achievable flow) without successful return of desirable membrane performance, an alert may be issued or therapy may continue; e.g., as described above. Systems that do not employ dialysate may use collected ultrafiltrate or removed fluid as a backwash in a similar manner to dialysate described above. Alternatively or in addition, replacement fluid may be redirected to perform backwashing for hemofiltration or the like.

Another corrective action that may be taken to prevent further fouling a membrane is to increase, to acceptable limits, the concentration of an anticoagulant, such as heparin, citrate, or the like, in the blood or dialysate. Of course, blood having too high a concentration of anticoagulant should not be returned to the patient. Alternatively or in addition, a thrombolytic agent, such as tissue plasminogen activator, streptokinase, reteplase or the like, may be added to clear or de-foul the membrane. However, such thrombolytic agents generally should not be introduced into the patient's circulation. Accordingly, blood may be diverted or blood flow stopped (if the thrombolytic agent is in dialysate) during thrombolytic agent use or high concentration anticoagulant usage. After the membrane is cleared, anticoagulant concentration may be reduced (or thrombolytic agent use ceased) and blood flow resumed or redirected back to the patient.

In embodiments, vascular access may be monitored in accordance with the teachings presented herein. Changes in the access (e.g., catheter, fistula or graft) can cause poor performance because of inadequate flow or recirculation. Flow could be monitored as described herein and related to the pump set-point or pressure. If differences are substantial, poor access flow could be determined to be the result or a likely result. Recirculation may be monitored by measuring the membrane performance for waste removal and comparing to the actual waste removal from the patient. If the membrane performance is within predetermined limits, then the likelihood that recirculation in the access is occurring may be high.

In embodiments, a system may include one or more blood flow sensors 200F, 200G positioned and configured to monitor blood flow, or an indicator thereof, into the system (e.g., via sensor 200F) or through the system (e.g., via sensor 200G). As discussed above, blood flow rate from the patient change or vary due to a variety of factors, such as needle placement, patient condition variability, blood line variability, etc. If blood flow rate detected by sensor 200F is too high or too low, control electronics 150 which are operably coupled to sensor 200F, may instruct blood flow control element 120 to alter the rate of flow of blood flow through the system. The rate of blood flow through the system may be detected by, e.g., sensor 200G, which is operably coupled to control electronics 150. If a desired rate of flow through the system is not achieved or achievable, one or more system parameters, such as dialysate flow rate, pressure differential across membrane 135, or the like, may be modified. Alternatively, or in addition, one or more session parameters, such as session time, may be adjusted in light of the monitored blood flow rate.

While the device discussed with regard to FIGS. 5-6 includes a medium component 130 that contains a membrane 135, it will be understood that many of the sensors and control components discussed above may be applied with a medium that employs a sorbent.

It will also be understood that some components may be located external to device 100. In some embodiments, the control electronics (e.g., processor, memory, algorithm) for determining whether the sensed data is indicative of the medium (e.g., membrane, sorbent, etc.) operating within acceptable parameters are located outside of the device 100 and are in communication with the device and may instruct the device to take appropriate action (e.g., alter pressure across membrane to alter fluid removal rate, backwash, etc.). In some embodiments, the alert circuitry and components are located outside of device 100.

It will be understood that the blood fluid removal devices and systems, and components thereof, described herein are presented for purposes of illustration and not limitation. Components, devices and systems other than those described herein, or derivations of the components, devices and systems described herein, may be employed. Further, components of the devices depicted and discussed above may be interchanged, substituted, omitted or added to components of alternative embodiments, as appropriate. Further, it will be understood that, while many of the blood fluid removal devices depicted in a variety of the figures, such as FIGS. 1-4, are shown as external to the patient, the teachings presented herein apply if the device, or components thereof, were implanted in the patient.

The devices and systems described above, or components thereof, may be used to carry out the methods depicted in FIGS. 7-11 and described below, or portions thereof. Of course, any suitable device or system may be employed to carry out the methods, or portions thereof, described below. It will be understood that various steps of the methods presented with regard to any one of FIGS. 7-11 below may be interchanged, substituted, omitted or added to steps presented with regard to any other of FIGS. 7-11.

Figure 7:
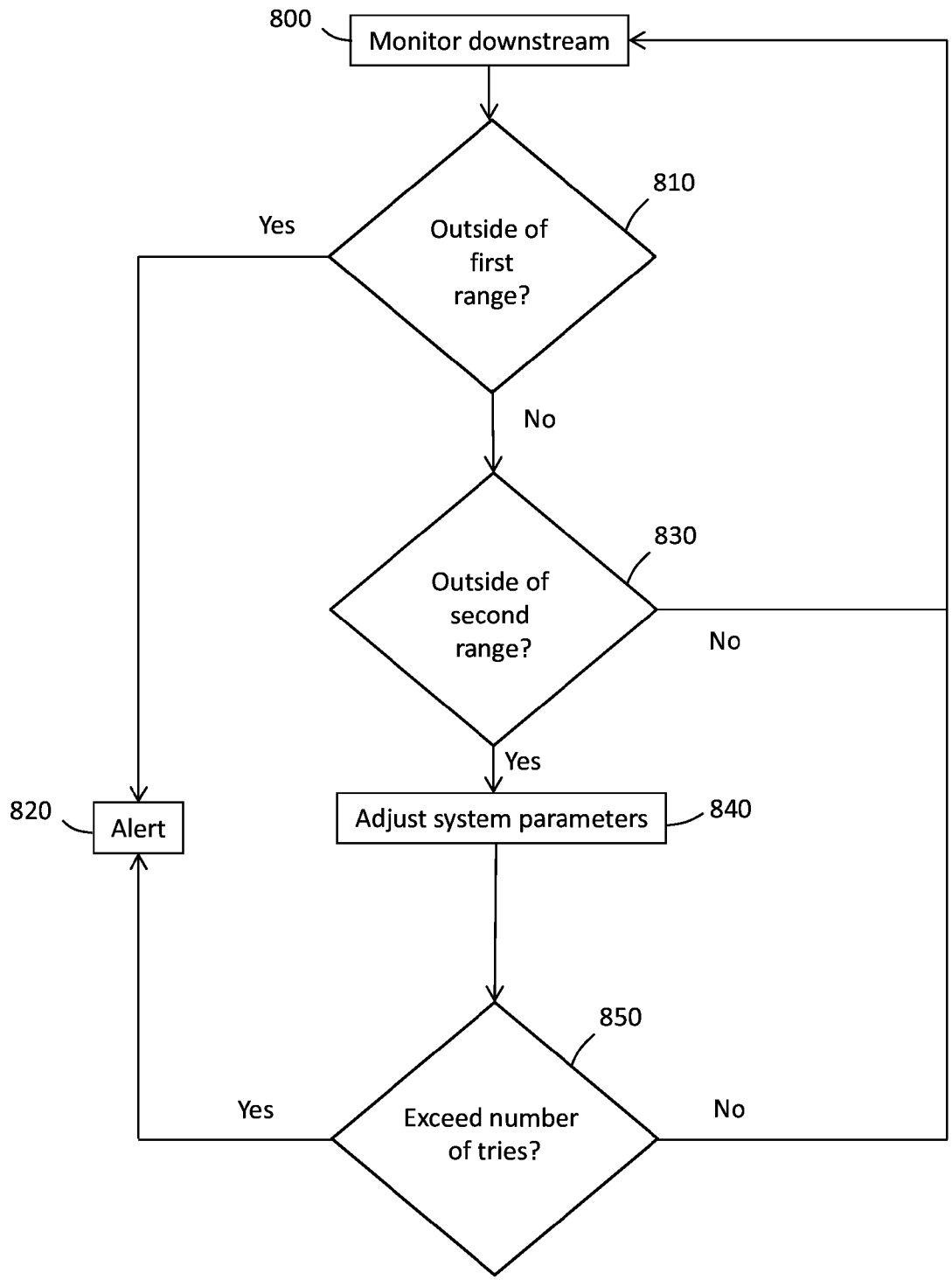
FIGS. 7-11 are flow diagrams illustrating overviews of general methods in accordance with embodiments described herein.

Referring now to FIG. 7, an example of a method for monitoring the performance of a blood fluid removal medium of a blood fluid removal device is shown. The method includes monitoring a condition downstream of the medium (800). The condition may be, for example, flow rate of fluid exiting the medium, the concentration of a compound (e.g., waste product) in fluid or blood exiting the medium, or the like. The depicted method includes determining whether a value of the monitored condition is outside of a first heightened range. If the value of the monitored parameter is outside of the first range (e.g. upper limit), an alert may be issued (820). If the value is not outside of the first heightened range, a determination as to whether the value of the monitored condition is outside of a second less heightened range (830). If the value is not outside of the second range, monitoring (800) may continue. If the value is determined to be outside the second range (e.g., lower limit), one or more system parameters, such as blood flow rate, dialysate flow rate, negative pressure application, or the like, may be adjusted (840) and monitoring (800) may continue. In some cases, it may be desirable to limit the number of attempts to adjust system parameters (840) to bring the medium performance within a desired range. If a predetermined number of tries is exceeded (850) or set amount of time passes without bring the medium performance within a desired range (i.e., within the second range, 830), an alert may be issued (820).

Figure 8:
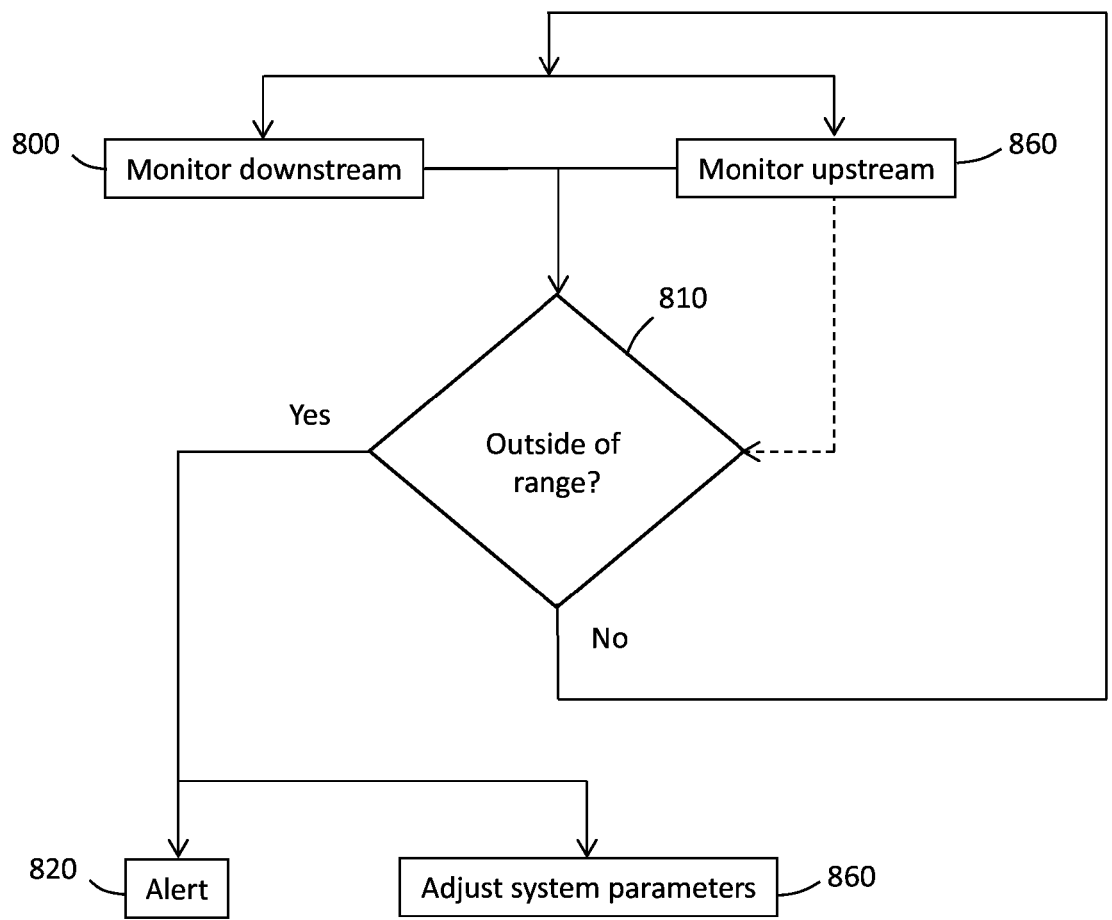

Referring now to FIG. 8, a method for monitoring the performance of a blood fluid removal medium of a blood fluid removal device that employs monitoring downstream (800) and upstream (860) of the medium is shown. The upstream monitoring (860) may include monitoring flow rate of blood, pressure, or concentration of a compound, such as a waste product, in blood before the blood enters the medium. A value of the upstream monitoring may be used in determining what constitutes and appropriate range of medium performance (810). In the depicted embodiment, values associated with the upstream (860) and downstream (800) monitoring are compared and a determination is made as to whether the compared values are indicative of the medium performance being out of range (810). If the values are determined not to be indicative of medium performance being out of range (e.g., fouled, inefficient removal of waste product or fluid, etc.), monitoring (800, 860) may continue (e.g., as discussed above with regard to FIG. 7). If the values are determined to be indicative of medium performance being out of range, an alert may be issued (820).

Figure 9:
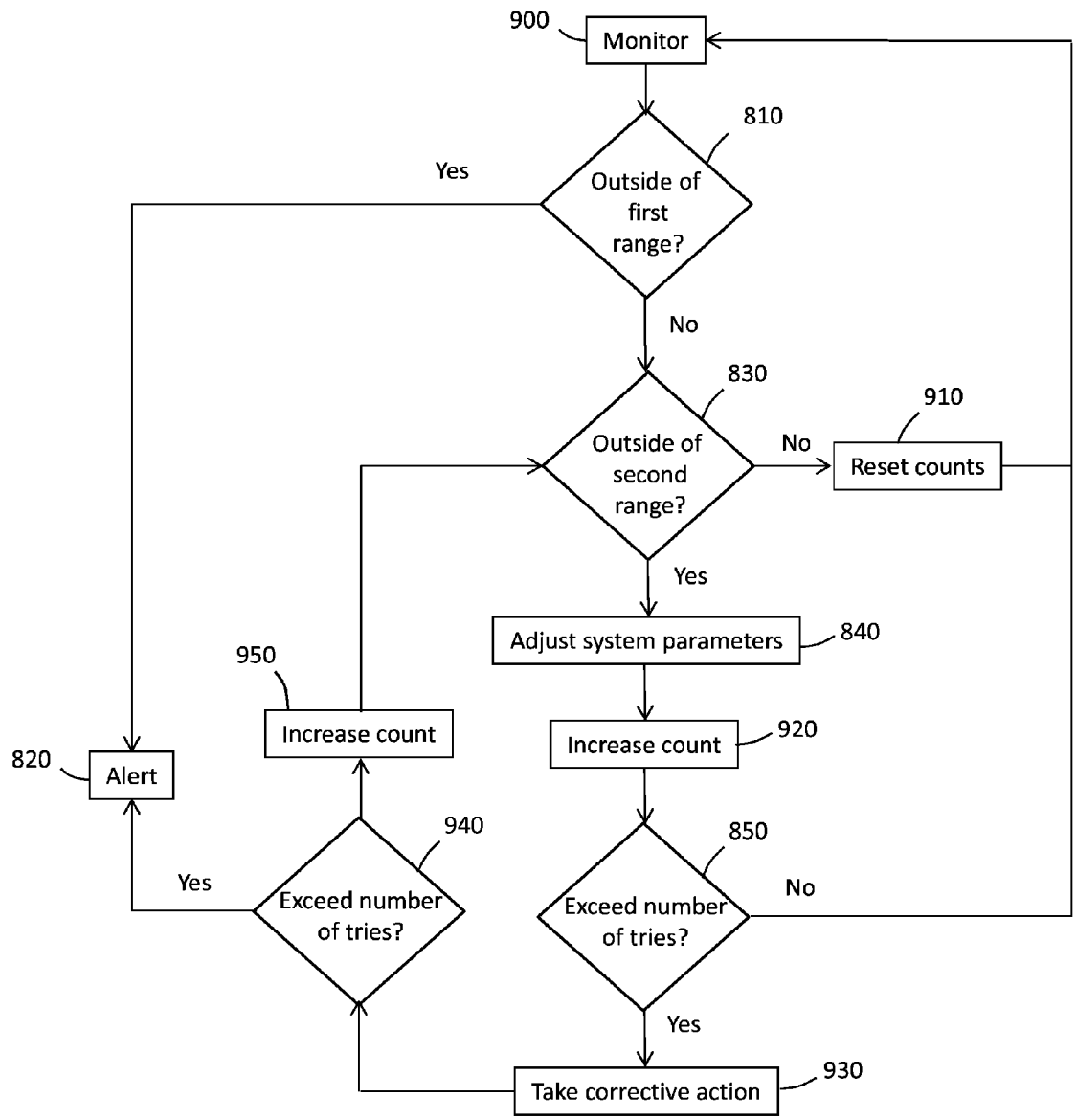

Referring now to FIG. 9 a method is shown, which includes attempting to maintain or return system parameter values to values within a desired range and taking corrective action if the values do not return to the desired range. Of course, aspects of these methods may be performed independently if desired. In the depicted embodiment, a system parameter is monitored (900). The monitoring may be upstream of the medium, downstream of the medium, or within the medium. If a value of the monitored parameter is outside of a first range (810), which may be indicative of more serious system inefficiency or malfunction, an alert (820) may be issued. If the value of the system parameter is determined not to be outside of the first range (810), a determination may be made as to whether the parameter is outside of a second range (830), which may be indicative of a less serious inefficiency or malfunction. If the value is not outside of the second range (i.e., the system is performing as expected), counts (910) may be reset, and monitoring (900) may continue. Additional detail regarding resetting counts (910), which refers to attempts to adjust system parameters so that monitored values will fall within desired ranges and attempts to correct a cause or source of system inefficiencies or malfunctions, will be discussed below.

If the monitored value is determined to be outside of the second range (820), an attempt at modifying or adjusting system parameters (840) may be made to return system performance to desired levels (e.g., monitored values fall within second range), e.g., as discussed above with regard to FIG. 7. Before or after adjusting the system parameters (840) a count of the number of corrective attempts may be increased (920). Alternatively or in addition, a timer may be started. A determination may then be made as to whether the number of attempts or time has been exceeded (850). If the number of tries has been exceeded, corrective action may be taken (930) in an attempt to address a cause or source of the malfunction. By way of example, actions may be taken to de-foul or clean a membrane. Examples of how this may be done are presented below with regard to FIG. 10. A determination may be made as to whether a preset number of tries (or time) to address a cause or source of the system inefficiency or malfunction has been attempted (940). If the number of tries has been exceeded, an alert may be issued (820). The count of the number of tries (950) may be increased at any point after taking corrective action (930). If the count or time does not exceed the preset count or time, a determination may be made as to whether the corrective action resulted in the monitored values returning to within the second range (900). If yes, the counts (i.e., counts 920 and 950) may be reset.

Figure 10:
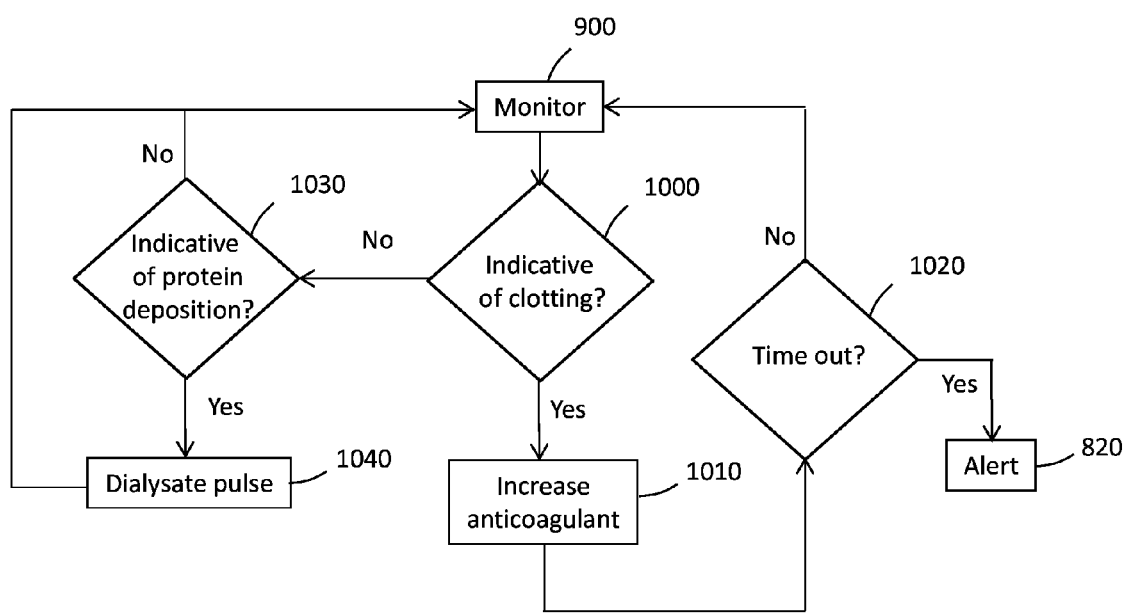

Referring now to FIG. 10, an example of a method for detecting an underperforming membrane or medium and for cleaning or de-fouling the membrane or medium is shown. Severity of fouling of a membrane or medium in contact with blood is most often due to depositing of proteins or clotting factors on the medium, which can lead to blood clotting on medium. During initial protein deposition, medium performance should not be significantly compromised. However, as more protein deposits or initial clotting develops, the performance of the medium will further deteriorate until significant clotting or protein deposition renders the medium ineffective.

FIG. 10 depicts a method in which the medium includes a membrane and the system employs dialysate, such as with a hemodialysis system. However, it will be understood that similar methods may be employed in other types of systems and other types of media; e.g. sorbents. As indicated in FIG. 10, membrane performance can be monitored (900); e.g. as discussed above with regard to pressure differential, flow rates, concentration of chemical species, etc. A determination may be made as to whether a monitored value is indicative of clotting (1000); e.g., a high level of membrane inefficiency. If yes, an increase in anticoagulant agent may be added to the blood or dialysate (1010) in an attempt to prevent further clot formation or a thrombolytic agent may be added to dissolve the clot. As discussed above, it may be desirable to stop blood flow or divert blood flow during times thrombolytic agents are being employed. If the monitored value remains indicative of clotting after a predetermined amount of time (1020) after administration of increased concentrations of anticoagulant or thrombolytic agent (or after sequential increases in anticoagulant reach a predetermined upper limit), an alert may be issued (820). If, however, the monitored value is not indicative of clotting, a determination may be made as to whether the monitored value is indicative of a predetermined degree of protein deposition (1030), and a pulse of dialysate (1040), sustained increased dialysate flow or the like, may be delivered in an attempt to clear the deposited proteins from the membrane, and the process repeated.

It will be understood that the order of the steps in FIG. 10 are shown only for purposes of illustration and that the method may be performed in any other suitable order (e.g., step 1030 may be performed before step 1000). Media, such as membranes, or systems may be readily calibrated by one of skill in the art such that changes in monitored values can be attributed to certain degrees of fouling.

Figure 11:
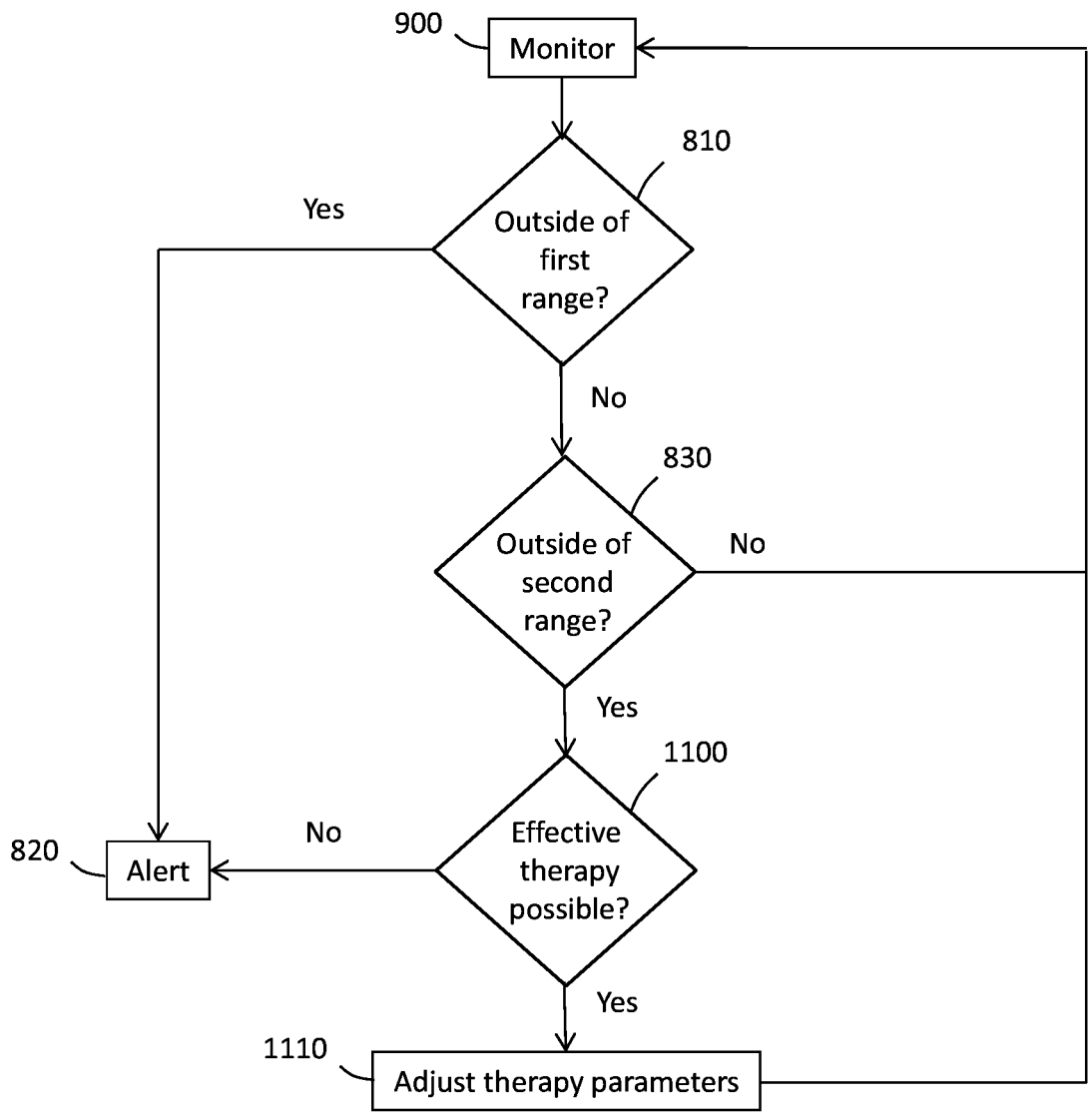

Referring now to FIG. 11, a method is depicted in which therapy proceeds despite monitored parameters indicating poor system performance. In the depicted embodiment, a system parameter is monitored (900). The monitoring may be upstream of the medium, downstream of the medium, or within the medium or medium chamber. If a value of the monitored parameter is outside of a first range (810), which may be indicative of more serious system inefficiency or malfunction, an alert (820) may be issued. If the value of the system parameter is determined not to be outside of the first range (810), a determination may be made as to whether the parameter is outside of a second range (830), which may be indicative of a less serious inefficiency or malfunction. If the value is not outside of the second range (i.e., the system is performing as expected) monitoring (900) and therapy may continue. If, however, the value is outside of the second range (830), a determination may be made as to whether effective therapy may be delivered (1100) despite the poor system performance (as measured by the monitored parameter). For example, it may be determined that the medium is not performing efficiently (e.g., slow rate of waste product or fluid removal from blood), but that an extended session time may be acceptable for achieving therapeutic goals. The therapy parameters may be adjusted (1110); e.g., extend session time, and the process continued.

As discussed above with regard to FIG. 11, therapy may continue despite poor system performance in some cases. In embodiments, a method as described in, or similar to, FIG. 11 may be combined with a method as described in, or similar to, FIG. 7 or 8, where the system attempts to adjust parameters to return the monitored values to desired ranges and continues to deliver therapy with adjusted therapy parameters such attempts.

The methods described herein, including the methods depicted in FIGS. 7-11, may be carried out by sensor devices, blood fluid removal devices, or other devices in communication with sensor devices or blood fluid removal devices. These methods may be algorithms or instructions programmed into memory of such devices, which may be carried out by processors or other control electronics of the devices. Preferably, the processor is in communication with appropriate control elements of the device and is configured to control such elements in a manner such that the programmed instructions are carried out by the appropriate device. It will be understood that a computer readable medium programmed with instructions that cause a sensor device, blood fluid removal device, or other suitable device to carry out a method, or a portion thereof, as described herein are contemplated. The computer readable medium may be non-transitory, i.e. lasting for more than a fleeting instant or seconds. The medium may be memory, such as RAM or ROM, a cd or dvd, flash memory, or the like.

Various aspects of methods, systems, computer-readable media, and the like are described herein. A non-limiting summary of some of the aspects is presented below.

In a first aspect, an ultrafiltration system comprises (i) a medium housing defining a major chamber; (ii) a blood fluid removal membrane disposed into the media housing and sealingly dividing the major chamber into first and second minor chambers; (iii) a first inlet and a first outlet in fluid communication with the first minor chamber, wherein the system is configured such that blood enters the first minor chamber through the first inlet and exits the first minor chamber though the first outlet; (iv) a second outlet in fluid communication with the second minor chamber, wherein the system is configured such that fluid removed from the blood exits the second minor chamber through the second outlet; (v) a first sensor configured to detect an indicator of fluid flow at or downstream of the second outlet; and control electronics configured to acquire data from the first sensor and configured to determine whether the membrane is functioning within predetermined parameters based on the acquired data.

A second aspect is a system of the first aspect, further comprising a control element configured to adjust the pressure differential between the first minor chamber and the second minor chamber, and wherein the control electronics are further configured to cause the control element to adjust the pressure differential based on the data acquired from the sensor.

A third aspect is a system of the first or second aspect, further comprising an alert circuit configured to alert a patient or a healthcare provider, wherein the control electronics are configured to activate the alert circuit if the control electronics determine that membrane is not functioning within the predetermined parameters.

A fourth aspect is a system of any of aspects 1-3, further comprising a second sensor configured to detect an indicator of flow rate at or upstream of the first inlet or at or downstream of the first outlet, wherein the control electronics are configured to acquire data from the second sensor, and wherein the control electronics are configured to determine whether the membrane is functioning within predetermined parameters based on the data acquired from the first and second sensors.

A fifth aspect is blood fluid removal system comprising: (i) a medium housing defining a major chamber; (ii) a blood fluid removal membrane disposed into the media housing and sealingly dividing the major chamber into first and second minor chambers; (iii) a first inlet and a first outlet in fluid communication with the first minor chamber, wherein the system is configured such that blood enters the first minor chamber through the first inlet and exits the first minor chamber though the first outlet; (iv) a second outlet in fluid communication with the second minor chamber, wherein the system is configured such that fluid removed from the blood exits the second minor chamber through the second outlet; (v) a first sensor configured to detect an indicator of a blood waste product or fluid flow at or downstream of the second outlet; and (vi) control electronics configured to acquire data from the sensor and configured to determine whether the membrane is functioning within predetermined parameters based on the acquired data.

A sixth aspect is a system of the fifth aspect, further comprising a control element configured to adjust the pressure differential between the first minor chamber and the second minor chamber, and wherein the control electronics are further configured to cause the control element to adjust the pressure differential based on the data acquired from the first sensor.

A seventh aspect is a system of the fifth or sixth aspect, further comprising an alert circuit configured to alert a patient or a healthcare provider, wherein the control electronics are configured to activate the alert circuit if the control electronics determine that membrane is not functioning within the predetermined parameters.

An eighth aspect is a system of any of aspects 5-7, further comprising a second sensor configured to detect the indicator of a blood waste product or fluid flow at or upstream of the first inlet, wherein the control electronics are configured to acquire data from the second sensor, and wherein the control electronics are configured to compare data acquired from the first sensor to data acquired from the second sensor in determining whether the membrane is functioning within predetermined parameters.

A ninth aspect is a system of any of aspects 1-8, further comprising (i) a second inlet in communication with the second minor chamber, wherein dialysate is configured to flow through the second inlet and the second outlet; and (ii) a dialysate flow controller operably coupled to the control electronics, wherein control electronics are configured to increase dialysate flow rate, via the dialysate flow controller, through the second minor chamber if the membrane is determined not to be functioning within predetermined limits.

A tenth aspect is a blood fluid removal system comprising: (i) a medium housing defining a major chamber; (ii) a blood fluid removal membrane disposed into the media housing and sealing dividing the major chamber into first and second minor chambers; (iii) a first inlet and a first outlet in fluid communication with the first minor chamber, wherein the system is configured such that blood enters the first minor chamber through the first inlet and exits the first minor chamber though the first outlet; (iv) a second outlet in fluid communication with the second minor chamber, wherein the system is configured such that fluid removed from the blood exits the second minor chamber through the second outlet; (v) a first sensor configured to detect an indicator of a blood waste product at or upstream of the first inlet; (vi) a second sensor configured to detect the indicator of the blood waste product at or downstream of the first outlet; and control electronics configured to acquire data from the sensor and configured to determine whether the membrane is functioning within predetermined parameters based on the acquired data.

An eleventh aspect is a system of the tenth aspect, further comprising a control element configured to adjust the pressure differential between the first minor chamber and the second minor chamber, and wherein the control electronics are further configured to cause the control element to adjust the pressure differential based on the data acquired from the first sensor.

A twelfth aspect is a system of the tenth or eleventh aspect, further comprising an alert circuit configured to alert a patient or a healthcare provider, wherein the control electronics are configured to activate the alert circuit if the control electronics determine that membrane is not functioning within the predetermined parameters.

A thirteenth aspect is a system of any of aspects 9-12, further comprising (i) a second inlet in communication with the second minor chamber, wherein dialysate is configured to flow through the second inlet and the second outlet; and (ii) a dialysate flow controller operably coupled to the control electronics, wherein control electronics are configured to increase dialysate flow rate, via the dialysate flow controller, through the second minor chamber if the membrane is determined not to be functioning within predetermined limits.

A fourteenth aspect is a blood fluid removal system comprising: (i) a medium housing having an inlet and an outlet; (ii) a sorbent configured to adsorb one or more components of blood disposed into the media housing, wherein the system is configured such that a patient's enters the media housing through the inlet and exits the housing via the outlet; (iii) a sensor configured to detect an indicator of fluid flow at or downstream of the outlet; and (iv) control electronics configured to acquire data from the sensor and configured to determine whether the sorbent is functioning within predetermined parameters based on the acquired data.

A fifteenth aspect is a system of aspect 14, further comprising an alert circuit configured to alert a patient or a healthcare provider, wherein the control electronics are configured to activate the alert circuit if the control electronics determine that the sorbent is not functioning within the predetermined parameters.

A sixteenth aspect is a blood fluid removal system comprising: (i) a medium housing having an inlet and an outlet; (ii) a sorbent configured to adsorb one or more components of blood disposed into the media housing, wherein the system is configured such that a patient's enters the media housing through the inlet and exits the housing via the outlet; (iii) a first sensor configured to detect an indicator of a blood waste product at or downstream of the outlet; and (iv) control electronics configured to acquire data from the first sensor and configured to determine whether the sorbent is functioning within predetermined parameters based on the acquired data.

A seventeenth aspect is a system of aspect 16, further comprising an alert circuit configured to alert a patient or a healthcare provider, wherein the control electronics are configured to activate the alert circuit if the control electronics determine that sorbent is not functioning within the predetermined parameters.

An eighteenth aspect is a system of aspect 16 or claim 17, further comprising a second sensor configured to detect the indicator of the blood waste product at or upstream of the inlet, wherein the control electronics are configured to acquire data from the second sensor, and wherein the control electronics are configured to compare data acquired from the first sensor to data acquired from the second sensor in determining whether the sorbent is functioning within predetermined parameters.

A nineteenth aspect is a method for monitoring blood fluid removal medium performance of a blood fluid removal system, wherein the method is carried out by the system, the system configured such that untreated blood enters or contacts the medium and removed fluid or treated blood exit or leave the medium, the method comprising: (i) monitoring an indicator of a level of a compound in removed fluid or treated blood downstream of the medium; and (ii) determining whether the medium is performing within predetermined parameters based a value of the monitored indicator.

A twentieth aspect is a method of aspect 19, further comprising monitoring an indicator of a level of the compound in untreated blood upstream of the medium.

A twenty-first aspect is a method of aspect 20, wherein determining whether the medium is performing within predetermined parameters comprises comparing a value of the monitored indicator obtained upstream of the medium to the value of the monitored indicator obtained downstream of the medium A twenty-second aspect is a method of aspect 20, wherein determining whether the medium is performing within predetermined parameters comprises comparing a value of the monitored indicator obtained upstream of the medium to the value of the monitored indicator obtained downstream of the medium based on the value of the monitored indicator obtained upstream of the medium.

A twenty-third aspect is a system comprising: (i) a blood fluid removal medium having an inlet for receiving untreated blood, an outlet through which treated blood is configured to exit, and an outlet through which fluid removed from the blood is configured to exit; (ii) a first sensor downstream of the medium and configured to monitoring an indicator of a level of a compound in removed fluid or treated blood; and (iii) control electronics in communication with the first sensor, wherein the control electronics are configured to carry out the method of aspect 19

A twenty-fourth aspect is a system of aspect 23, further comprising a computer readable medium that, when executed by the control electronics, cause the control electronics to carry out the method of aspect 19.

A twenty-fifth aspect is a system comprising: (i) a blood fluid removal medium having an inlet for receiving untreated blood, an outlet through which treated blood is configured to exit, and an outlet through which fluid removed from the blood is configured to exit; (ii) a first sensor downstream of the medium and configured to monitoring an indicator of a level of a compound in removed fluid or treated blood; (iii) a second sensor upstream of the medium and configured to monitor an indicator of a level of the compound in the untreated blood; (iv) control electronics in communication with the first and second sensors, wherein the control electronics are configured to carry out the method of any of aspects 19-21.

A twenty-sixth aspect is a method for monitoring blood fluid removal medium performance of a blood fluid removal system, the system configured such that untreated blood enters the medium and removed fluid and treated blood exit the medium, the method comprising: (i) monitoring an indicator of a flow rate of removed fluid downstream of the medium; and (ii) determining whether the medium is performing within predetermined parameters based a value of the monitored indicator.

A twenty-seventh aspect is method of aspect 26, further comprising monitoring an indicator of a flow rate of untreated blood upstream of the medium.

A twenty-eighth aspect is a method of aspect 27, wherein determining whether the medium is performing within predetermined parameters comprises comparing a value of the monitored indicator obtained upstream of the medium to the value of the monitored indicator obtained downstream of the medium.

A twenty-ninth aspect is a method of aspect 28, wherein determining whether the medium is performing within predetermined parameters comprises comparing a value of the monitored indicator obtained upstream of the medium to the value of the monitored indicator obtained downstream of the medium based on the value of the monitored indicator obtained upstream of the medium.

A thirtieth aspect is a system comprising: (i) a blood fluid removal medium having an inlet for receiving untreated blood, an outlet through which treated blood is configured to exit, and an outlet through which fluid removed from the blood is configured to exit; (ii) a first sensor downstream of the medium and configured to monitoring a flow rate of removed fluid; (iii) and control electronics in communication with the first sensor, wherein the control electronics are configured to carry out the method of aspect 26.

A thirty-first aspect is a system of aspect 29, further comprising a computer readable medium that, when executed by the control electronics, cause the control electronics to carry out the method of aspect 26.

A thirty-second aspect is a system comprising: (i) a blood fluid removal medium having an inlet for receiving untreated blood, an outlet through which treated blood is configured to exit, and an outlet through which fluid removed from the blood is configured to exit; (ii) a first sensor downstream of the medium and configured to monitoring an indicator of a level of a compound in removed fluid or treated blood; (iii) a second sensor upstream of the medium and configured to monitor an indicator of a level of the compound in the untreated blood; and (iv) control electronics in communication with the first and second sensors, wherein the control electronics are configured to carry out the method of any of aspects 26-28.

A thirty-third aspect is a system of aspect 32, further comprising a computer readable medium that, when executed by the control electronics, cause the control electronics to carry out the method of any of aspects 26-28.

A thirty-fourth aspect is a blood fluid removal system comprising: (i) a medium housing defining a major chamber; (ii) a blood fluid removal membrane disposed into the media housing and sealingly dividing the major chamber into first and second minor chambers; (iii) a first inlet and a first outlet in fluid communication with the first minor chamber, wherein the system is configured such that blood enters the first minor chamber through the first inlet and exits the first minor chamber though the first outlet; (iv) a second inlet and a second outlet in fluid communication with the second minor chamber, wherein the system is configured such that fluid removed from the blood exits the second minor chamber through the second outlet and such that dialysate flows through the second minor chamber from the second inlet to the second outlet; (v) one or more sensors configured to measure a pressure differential across the membrane; (vi) control electronics configured to acquire data from the one or more sensors and configured to determine whether the membrane is functioning within a first predefined range of parameters based on the acquired data; and (vii) a dialysate flow controller operably coupled to the control electronics, wherein the control electronics are configured to increase dialysate flow rate through the second minor chamber, via control of the dialysate flow controller, if the membrane is determined to not be function within the first range.

A thirty-fifth aspect is a blood fluid removal system of aspect 34, wherein the control electronics are further configured to acquire data from the one or more sensors and to determine whether the membrane is functioning within a first predefined range of parameters based on the acquired data at a predetermined amount of time after the dialysate flow rate is increased.

A thirty-sixth aspect is a blood fluid removal system of aspect 34, wherein the control electronics configured (i) to reduce the rate of the dialysate through the second minor chamber at a predetermined time after the flow rate is increased, and (ii) to acquire data from the one or more sensors after the dialysate rate has been reduced and to determine whether the membrane is functioning within a first predefined range of parameters based on the acquired data after the flow rate has been reduced.

A thirty-seventh aspect is a blood fluid removal system comprising: (i) a medium housing defining a major chamber; (ii) a blood fluid removal membrane disposed into the media housing and sealingly dividing the major chamber into first and second minor chambers; (iii) a first inlet and a first outlet in fluid communication with the first minor chamber, wherein the system is configured such that blood enters the first minor chamber through the first inlet and exits the first minor chamber though the first outlet; (iv) a second inlet and a second outlet in fluid communication with the second minor chamber, wherein the system is configured such that fluid removed from the blood exits the second minor chamber through the second outlet and such that dialysate flows through the second minor chamber from the second inlet to the second outlet; (v) one or more sensors configured to measure a pressure differential across the membrane; (vi) a dialysate flow controller configured to control the rate of dialysate flow rate through the second minor chamber; (vii) control electronics operably coupled to the one or more sensors and to the dialysate flow controller; and (viii) a computer-readable medium comprising instructions that, when implemented, cause the control electronics (i) to acquire data from the one or more sensors, (ii) determine whether the membrane is functioning within a first predefined range of parameters based on the acquired data; and (iii) increase dialysate flow rate through the second minor chamber, via control of the dialysate flow controller, if the membrane is determined to not be function within the first range.

A thirty-eighth aspect is a blood fluid removal system of aspect 37, wherein the computer readable medium further comprises instructions that, when implemented, cause the control electronics (i) to acquire data from the one or more sensors, (ii) and to determine whether the membrane is functioning within a first predefined range of parameters based on the acquired data at a predetermined amount of time after the dialysate flow rate is increased.

A thirty-ninth aspect is a blood fluid removal system of aspect 37, wherein the computer readable medium further comprises instructions that, when implemented, cause the control electronics (i) to reduce the rate of the dialysate through the second minor chamber at a predetermined time after the flow rate is increased, (ii) to acquire data from the one or more sensors after the dialysate rate has been reduced, and (iii) to determine whether the membrane is functioning within a first predefined range of parameters based on the acquired data after the flow rate has been reduced.

A fortieth aspect is a method for de-fouling a membrane of a blood fluid removal system, the system comprising (i) a medium housing defining a major chamber; (ii) a blood fluid removal membrane disposed into the media housing and sealingly dividing the major chamber into first and second minor chambers; (iii) a first inlet and a first outlet in fluid communication with the first minor chamber, wherein the system is configured such that blood enters the first minor chamber through the first inlet and exits the first minor chamber though the first outlet; (iv) a second inlet and a second outlet in fluid communication with the second minor chamber, wherein the system is configured such that fluid removed from the blood exits the second minor chamber through the second outlet and such that dialysate flows through the second minor chamber from the second inlet to the second outlet; (v) one or more sensors configured to measure a pressure differential across the membrane; (vi) a dialysate flow controller configured to control the rate of dialysate flow rate through the second minor chamber; and (vii) control electronics operably coupled to the one or more sensors and to the dialysate flow controller, the method carried out by the control electronics of the system and comprising: (i) acquiring data from the one or more sensors; (ii) determining whether the membrane is functioning within a first predefined range of parameters based on the acquired data; and (iii) increasing dialysate flow rate through the second minor chamber, via control of the dialysate flow controller, if the membrane is determined to not be function within the first range.

A forty-first aspect is a method of aspect 40, further comprising: (i) acquiring data from the one or more sensors; and (ii) determining whether the membrane is functioning within a first predefined range of parameters based on the acquired data at a predetermined amount of time after the dialysate flow rate is increased.

A forty-second aspect is a method of aspect 40, further comprising: (i) reducing the rate of the dialysate through the second minor chamber at a predetermined time after the flow rate is increased; (ii) acquiring data from the one or more sensors after the dialysate rate has been reduced; and (iii) determining whether the membrane is functioning within a first predefined range of parameters based on the acquired data after the flow rate has been reduced.

A forty-third aspect is a method comprising (i) monitoring rate of flow of blood, or an indicator thereof, entering a blood fluid removal device; (ii) determining whether the monitored flow rate or indicator is within a predetermined range; and (iii) adjusting a system parameter of the blood fluid removal device or a blood fluid removal session parameter if the monitored flow rate or indicator is not within the predetermined range.

A forty-fourth aspect is a method of the forty-third aspect, wherein the blood fluid removal device comprises a blood flow control element configured to control the rate of flow of blood through the device and wherein adjusting a system parameter comprises adjusting a parameter of a blood flow control element to adjust the rate of flow of blood through the device.

A forty-fifth aspect is a method of the forty-fourth aspect, further comprising (i) monitoring rate of flow of blood, or an indicator thereof, through the blood fluid removal device; and (ii) determining whether the monitored flow rate or indicator is within a predetermined range.

A forty-sixth aspect is a method of the forty-fifth aspect, wherein adjusting a system parameter comprises adjusting a parameter configured to control rate of fluid removal from the blood.

A forty-seventh aspect is a method according to the forty-sixth aspect, wherein adjusting the parameter configured to control rate of fluid removal from the blood comprises adjusting the rate of flow of dialysate.

A forty-eighth aspect is a method of the forty-sixth or forty-seventh aspect, wherein adjusting the parameter configured to control rate of fluid removal from the blood comprises adjusting a pressure differential across a medium configured to remove fluid from the blood.

A forty-ninth aspect is a method of any of aspects 46-48, wherein adjusting the session parameter comprises adjusting the length of time of the session.

Thus, systems, devices and methods for BLOOD FLUID REMOVAL SYSTEM PERFORMANCE MONITORING are described. Those skilled in the art will recognize that the preferred embodiments described herein may be altered or amended without departing from the true spirit and scope of the disclosure, as defined in the accompanying claims.

In the claims that follow, the designators "first", "second", "third" and the like are used for purposes of distinguishing between elements and not for purposes of enumerating the elements or for defining a sequence of the elements. For example, a "third" sensor does not necessarily imply that there are three sensors but rather that the "third" sensor is distinct from the "first" sensor. By way of further example, a "third" sensor does not necessarily come later in time than a "first" sensor.

What is claimed is:

1. A blood fluid removal system comprising:
   a medium housing defining a major chamber;
   a blood fluid removal membrane disposed into the media housing and sealingly dividing the major chamber into first and second minor chambers;
   a first inlet and a first outlet in fluid communication with the first minor chamber, wherein the system is configured such that blood enters the first minor chamber through the first inlet and exits the first minor chamber though the first outlet;
   a second outlet in fluid communication with the second minor chamber, wherein the system is configured such that fluid removed from the blood exits the second minor chamber through the second outlet;
   a first sensor configured to detect an indicator of a blood waste product or fluid flow at or downstream of the second outlet;
   control electronics configured to acquire data from the sensor and configured to determine whether the membrane is functioning within predetermined parameters based on the acquired data; and further comprising:
   (i) a second inlet in communication with the second minor chamber, wherein dialysate is configured to flow through the second inlet and the second outlet; and (ii) a dialysate flow controller operably coupled to the control electronics, wherein control electronics are configured to increase dialysate flow rate, via the dialysate flow controller, through the second minor chamber if the membrane is determined not to be functioning within predetermined limits.

2. A blood fluid removal system comprising:
   a medium housing defining a major chamber;
   a blood fluid removal membrane disposed into the media housing and sealingly dividing the major chamber into first and second minor chambers;
   a first inlet and a first outlet in fluid communication with the first minor chamber, wherein the system is configured such that blood enters the first minor chamber through the first inlet and exits the first minor chamber though the first outlet;
   a second inlet and a second outlet in fluid communication with the second minor chamber, wherein the system is configured such that fluid removed from the blood exits the second minor chamber through the second outlet and such that dialysate flows through the second minor chamber from the second inlet to the second outlet;
   one or more sensors configured to measure a pressure differential across the membrane;
   control electronics configured to acquire data from the one or more sensors and configured to determine whether the membrane is functioning within a first predefined range of parameters based on the acquired data; and
   a dialysate flow controller operably coupled to the control electronics, wherein the control electronics are configured to increase dialysate flow rate through the second minor chamber, via control of the dialysate flow controller, if the membrane is determined to not be function within the first range.

3. The blood fluid removal system of claim 2, wherein the control electronics are further configured to acquire data from the one or more sensors and to determine whether the membrane is functioning within a first predefined range of parameters based on the acquired data at a predetermined amount of time after the dialysate flow rate is increased.

4. The blood fluid removal system of claim 2, wherein the control electronics configured (i) to reduce the rate of the dialysate through the second minor chamber at a predetermined time after the flow rate is increased, and (ii) to acquire data from the one or more sensors after the dialysate rate has been reduced and to determine whether the membrane is functioning within a first predefined range of parameters based on the acquired data after the flow rate has been reduced.

5. A blood fluid removal system comprising:
   a medium housing defining a major chamber;
   a blood fluid removal membrane disposed into the media housing and sealingly dividing the major chamber into first and second minor chambers;
   a first inlet and a first outlet in fluid communication with the first minor chamber, wherein the system is configured such that blood enters the first minor chamber through the first inlet and exits the first minor chamber though the first outlet;
   a second inlet and a second outlet in fluid communication with the second minor chamber, wherein the system is configured such that fluid removed from the blood exits the second minor chamber through the second outlet and such that dialysate flows through the second minor chamber from the second inlet to the second outlet;
   one or more sensors configured to measure a pressure differential across the membrane;
   a dialysate flow controller configured to control the rate of dialysate flow rate through the second minor chamber;
   control electronics operably coupled to the one or more sensors and to the dialysate flow controller; and
   a computer-readable medium comprising instructions that, when implemented, cause the control electronics (i) to acquire data from the one or more sensors, (ii) determine whether the membrane is functioning within a first predefined range of parameters based on the acquired data; and (iii) increase dialysate flow rate through the second minor chamber, via control of the dialysate flow controller, if the membrane is determined to not be function within the first range.

6. The blood fluid removal system of claim 5, wherein the computer readable medium further comprises instructions that, when implemented, cause the control electronics (i) to acquire data from the one or more sensors, (ii) and to determine whether the membrane is functioning within a first predefined range of parameters based on the acquired data at a predetermined amount of time after the dialysate flow rate is increased.

7. The blood fluid removal system of claim 5, wherein the computer readable medium further comprises instructions that, when implemented, cause the control electronics (i) to reduce the rate of the dialysate through the second minor chamber at a predetermined time after the flow rate is increased, (ii) to acquire data from the one or more sensors after the dialysate rate has been reduced, and (iii) to determine whether the membrane is functioning within a first predefined range of parameters based on the acquired data after the flow rate has been reduced.

8. A method for de-fouling a membrane of a blood fluid removal system, the system comprising (i) a medium housing defining a major chamber; (ii) a blood fluid removal membrane disposed into the media housing and sealingly dividing the major chamber into first and second minor chambers; (iii) a first inlet and a first outlet in fluid communication with the first minor chamber, wherein the system is configured such that blood enters the first minor chamber through the first inlet and exits the first minor chamber though the first outlet; (iv) a second inlet and a second outlet in fluid communication with the second minor chamber, wherein the system is configured such that fluid removed from the blood exits the second minor chamber through the second outlet and such that dialysate flows through the second minor chamber from the second inlet to the second outlet; (v) one or more sensors configured to measure a pressure differential across the membrane; (vi) a dialysate flow controller configured to control the rate of dialysate flow rate through the second minor chamber; and (vii) control electronics operably coupled to the one or more sensors and to the dialysate flow controller, the method carried out by the control electronics of the system and comprising:
acquiring data from the one or more sensors;
determining whether the membrane is functioning within a first predefined range of parameters based on the acquired data; and
increasing dialysate flow rate through the second minor chamber, via control of the dialysate flow controller, if the membrane is determined to not be functioning within the first range.

9. The method of claim 8, further comprising:
acquiring data from the one or more sensors; and
determining whether the membrane is functioning within a first predefined range of parameters based on the acquired data at a predetermined amount of time after the dialysate flow rate is increased.

10. The method of claim 8, further comprising:
reducing the rate of the dialysate through the second minor chamber at a predetermined time after the flow rate is increased;
acquiring data from the one or more sensors after the dialysate rate has been reduced; and
determining whether the membrane is functioning within a first predefined range of parameters based on the acquired data after the flow rate has been reduced.

11. A method comprising:
monitoring rate of flow of blood, or an indicator thereof, entering the blood fluid removal system of claim 1;
determining whether the monitored flow rate or indicator is within a predetermined range; and
adjusting a system parameter of the blood fluid removal system or a blood fluid removal session parameter if the monitored flow rate or indicator is not within the predetermined range.

12. The method of claim 11, wherein the blood fluid removal system comprises a blood flow control element configured to control the rate of flow of blood through the system and wherein adjusting a system parameter comprises adjusting a parameter of a blood flow control element to adjust the rate of flow of blood through the system.

13. The method of claim 12, further comprising:
monitoring rate of flow of blood, or an indicator thereof, through the blood fluid removal system; and
determining whether the monitored flow rate or indicator is within a predetermined range.

14. The method of claim 13, wherein adjusting a system parameter comprises adjusting a parameter configured to control rate of fluid removal from the blood.

15. The method of claim 14, wherein adjusting the parameter configured to control rate of fluid removal from the blood comprises adjusting the rate of flow of dialysate.

16. The method of claim 14, wherein adjusting the parameter configured to control rate of fluid removal from the blood comprises adjusting a pressure differential across a medium configured to remove fluid from the blood.

17. The method of claim 14, wherein adjusting the session parameter comprises adjusting the length of time of the session.

18. The blood fluid removal system of claim 1, wherein the control electronics are further configured to acquire data from the sensor and to determine whether the membrane is functioning within predetermined parameters based on the acquired data at a predetermined amount of time after the dialysate flow rate is increased.

19. The blood fluid removal system of claim 1, further comprising a second sensor configured to detect the indicator of a blood waste product or fluid flow at or upstream of the second inlet, wherein the control electronics are configured to acquire data from the second sensor, and wherein the control electronics are configured to compare data acquired from the first sensor to data acquired from the second sensor in determining whether the membrane is functioning within predetermined parameters.

20. The blood fluid removal system of claim 1, further comprising a second sensor configured to detect the indicator of a blood waste product at or upstream of the first inlet, wherein the control electronics are configured to acquire data from the second sensor, and wherein the control electronics are configured to compare data acquired from the first sensor to data acquired from the second sensor in determining whether the membrane is functioning within predetermined parameters.

21. The blood fluid removal system of claim 1, wherein the wherein the control electronics are configured to acquire data from the sensor at a first time and at a second time later than the first time, and wherein the control electronics are configured to compare data acquired from the sensor at the first time and second time in determining whether the membrane is functioning within predetermined parameters.

22. The blood fluid removal system of claim 1, wherein, if the membrane is determined not to be functioning within predetermined limits, the control electronics are further configured to determine whether the data from the sensor is indicative of clotting, and to increase an amount of anticoagulants added to the blood or dialysate if the data from the sensor is indicative of clotting.

* * * * *